US008690882B2

(12) United States Patent
Pinczewski et al.

(10) Patent No.: US 8,690,882 B2
(45) Date of Patent: Apr. 8, 2014

(54) METHOD OF ARTHROPLASTY ON A KNEE JOINT AND APPARATUS FOR USE IN SAME

(75) Inventors: Leo Arich Pinczewski, Crows Nest (AU); Stephen John Parker, Mosman (AU); Greg Marik, Germantown, TN (US); Richard A. Rocco, Collierville, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 13/311,077

(22) Filed: Dec. 5, 2011

(65) Prior Publication Data
US 2012/0078262 A1    Mar. 29, 2012

Related U.S. Application Data

(60) Continuation of application No. 11/390,005, filed on Mar. 27, 2006, now Pat. No. 8,092,462, which is a division of application No. 10/238,953, filed on Sep. 10, 2002, now Pat. No. 7,371,240, which is a continuation of application No. PCT/AU01/00258, filed on Mar. 9, 2001.

(51) Int. Cl.
*A61B 17/58* (2006.01)
*A61B 17/60* (2006.01)
*A61F 2/00* (2006.01)

(52) U.S. Cl.
USPC .............................................. 606/88; 606/87

(58) Field of Classification Search
USPC .......... 606/87–90, 99, 105; 623/17.11–17.16, 623/20.31–20.36
See application file for complete search history.

(56) References Cited

U.S. PATENT DOCUMENTS

| 4,211,228 A | 7/1980 | Cloutier |
| 4,249,878 A | 2/1981 | Komarek |
| 4,457,307 A | 7/1984 | Stillwell |
| 4,524,766 A | 6/1985 | Peterson |

(Continued)

FOREIGN PATENT DOCUMENTS

| EP | 0 555 003 | 8/1993 |
| EP | 0 857 463 A2 | 8/1998 |

(Continued)

OTHER PUBLICATIONS

U.S. Appl. No. 11/615,045, Office Action mailed on Jul. 21, 2011, 13 pages.

(Continued)

*Primary Examiner* — Mary Hoffman
*Assistant Examiner* — Christina Negrellirodriguez
(74) *Attorney, Agent, or Firm* — Krieg DeVault LLP

(57) ABSTRACT

A method of, and apparatus for, arthroplasty of a knee joint comprising obtaining a desired spacing of the femur from the tibia by inserting a spacer into the knee joint between the femur and the tibia. The spacer is used as a reference for securing a guide jig in position about the knee joint for guiding resection of one or both of the femur and tibia for fitting of tibial and/or femoral prostheses. A method of resecting the femur while moving the tibia through an arc of motion to remove bone to the desired depth, a method of determining the position of the guide jig, the guide jog, an alignment device and the spacer are also described.

34 Claims, 25 Drawing Sheets

(56) References Cited

U.S. PATENT DOCUMENTS

| | | | |
|---|---|---|---|
| 4,574,794 | A | 3/1986 | Cooke et al. |
| 4,719,908 | A | 1/1988 | Averill et al. |
| 4,825,857 | A | 5/1989 | Kenna |
| 4,938,762 | A | 7/1990 | Wehrli |
| 5,100,409 | A | 3/1992 | Coates et al. |
| 5,122,144 | A | 6/1992 | Miller et al. |
| 5,171,244 | A | 12/1992 | Caspari et al. |
| 5,514,139 | A | 5/1996 | Goldstein et al. |
| 5,520,695 | A | 5/1996 | Luckman |
| 5,540,696 | A | 7/1996 | Booth, Jr. et al. |
| 5,597,379 | A | 1/1997 | Haines et al. |
| 5,643,272 | A | 7/1997 | Haines et al. |
| 5,702,460 | A | 12/1997 | Carls et al. |
| 5,735,904 | A | 4/1998 | Pappas |
| 5,749,876 | A | 5/1998 | Duvillier et al. |
| 5,755,803 | A | 5/1998 | Haines et al. |
| 5,810,827 | A | 9/1998 | Haines et al. |
| 5,824,098 | A | 10/1998 | Stein |
| 5,830,216 | A | 11/1998 | Insall et al. |
| 5,879,354 | A | 3/1999 | Haines et al. |
| 5,897,556 | A | 4/1999 | Drewry et al. |
| 5,968,050 | A * | 10/1999 | Torrie .............................. 606/87 |
| 6,013,081 | A | 1/2000 | Burkinshaw et al. |
| 6,056,754 | A | 5/2000 | Haines et al. |
| 6,132,468 | A | 10/2000 | Mansmann |
| 6,197,064 | B1 | 3/2001 | Haines et al. |
| 6,296,646 | B1 | 10/2001 | Williamson |
| 6,488,687 | B1 | 12/2002 | Masini |
| 6,632,225 | B2 | 10/2003 | Sanford et al. |
| 7,297,165 | B1 | 11/2007 | Kriek |
| 7,371,240 | B2 | 5/2008 | Pinczewski et al. |
| 2001/0001120 | A1 | 5/2001 | Masini |
| 2002/0029038 | A1 | 3/2002 | Haines |
| 2002/0198530 | A1 | 12/2002 | Sanford et al. |
| 2003/0130665 | A1 | 7/2003 | Pinczewski et al. |
| 2007/0239167 | A1 | 10/2007 | Pinczewski et al. |

FOREIGN PATENT DOCUMENTS

| | | |
|---|---|---|
| EP | 0 914 806 A1 | 5/1999 |
| FR | 2679766 | 2/1993 |
| JP | 63005739 | 1/1988 |
| WO | WO 91/10408 | 7/1991 |
| WO | WO 96/07361 | 3/1996 |
| WO | WO 01/66021 A1 | 9/2001 |
| WO | WO 01/66022 A1 | 9/2001 |

OTHER PUBLICATIONS

Notice of Reason for Refusal for Japanese Appl. No. 2001-564677, mailed Oct. 5, 2010, 4 pages.
Notice of Reason for Refusal for Japanese Appl. No. 2001-564677, mailed Aug. 9, 2011, 3 pages.
U.S. Appl. No. 11/615,045, Office Action mailed on Mar. 16, 2011, 20 pages.
U.S. Appl. No. 11/615,045, Response filed on Jun. 14, 2011, 21 pages.
Restriction Requirement dated Mar. 24, 2009 in related U.S. Appl. No. 11/615,045.
Response to Restriction Requirement filed Sep. 9, 2009 in related U.S. Appl. No. 11/615,045.
Office Action dated Oct. 4, 2010 in related European Patent Application No. 01911257.2.
Response to Final OA filed Sep. 9, 2010 in related U.S. Appl. No. 11/615,045.
Office Action dated Jun. 10, 2010 in related U.S. Appl. No. 11/615,045.
Response dated Apr. 28, 2010 in related U.S. Appl. No. 11/615,045.
U.S. Appl. No. 10/238,953 filed Sep. 10, 2002.
Office Action dated Sep. 23, 2004 in related U.S. Appl. No. 10/238,953.
Response dated Oct. 14, 2004 in related U.S. Appl. No. 10/238,953.
Response dated Jan. 26, 2005 in related U.S. Appl. No. 10/238,953.
Office Action dated Aug. 25, 2006 in related U.S. Appl. No. 10/238,953.
Response dated Dec. 1, 2006 in related U.S. Appl. No. 10/238,953.
Interview Summary dated Apr. 10, 2007 in related U.S. Appl. No. 10/238,953.
Response dated May 8, 2007 in related U.S. Appl. No. 10/238,953.
Office Action dated Jul. 27, 2007 in related U.S. Appl. No. 10/238,953.
Response dated Aug. 2, 2007 in related U.S. Appl. No. 10/238,953.
Advisory Action dated Sep. 27, 2007 in related U.S. Appl. No. 10/238,953.
Response dated Nov. 21, 2007 in related U.S. Appl. No. 10/238,953.
Notice of Allowance dated Jan. 8, 2008 in related U.S. Appl. No. 10/238,953.
Office Action dated Oct. 28, 2009 in related U.S. Appl. No. 11/615,045.

* cited by examiner

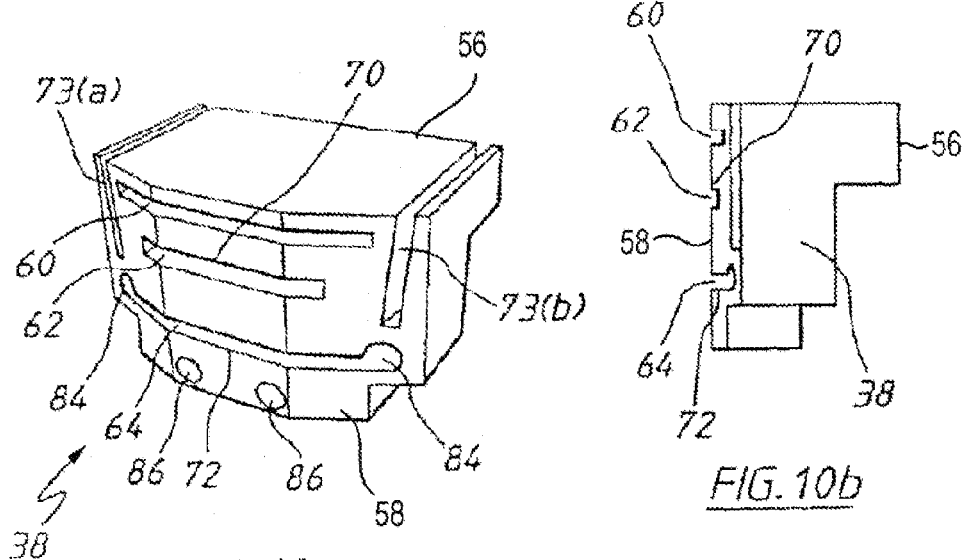
FIG. 10a
FIG. 10b
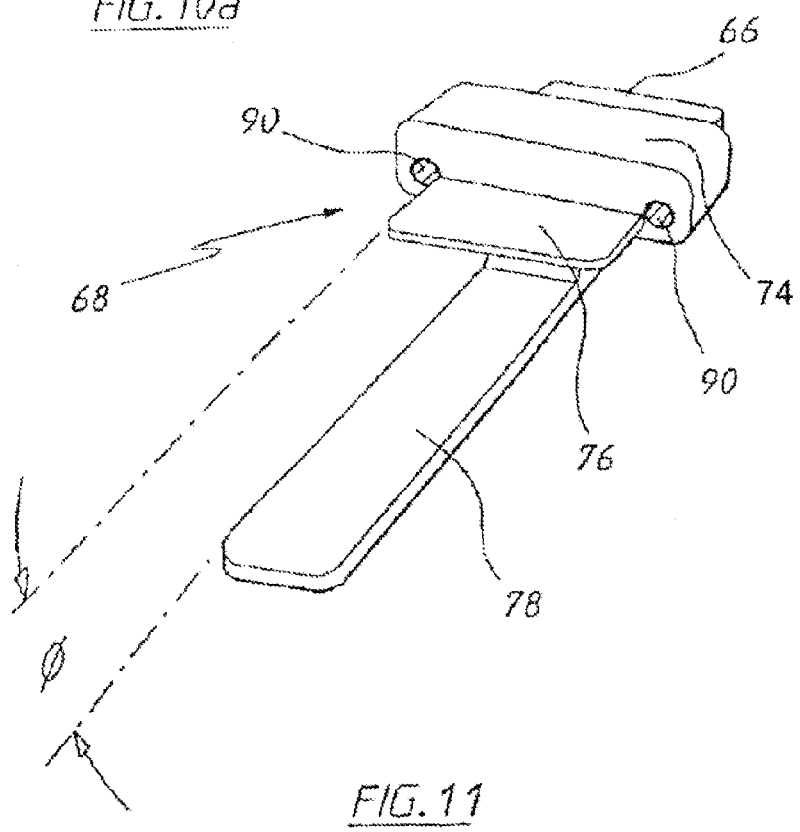
FIG. 11

METHOD OF ARTHROPLASTY ON A KNEE JOINT AND APPARATUS FOR USE IN SAME

CROSS-REFERENCE TO RELATED APPLICATIONS

This application is a continuation of U.S. patent application Ser. No. 11/390,005 filed on Mar. 27, 2006 now U.S. Pat. No. 8,092,462, which is a divisional of U.S. patent application Ser. No. 10/238,953 filed on Sep. 10, 2002 and issued as U.S. Pat. No. 7,371,240, which is a continuation of International Application No. PCT/AU01/00258 filed on Mar. 9, 2001 and published in English as International Publication Number WO 01/66021 A1 on Sep. 13, 2001, which claims priority to Australian Patent Application No. PQ 6161 filed on Mar. 10, 2000, Australian Patent Application No. PQ 8999 filed on Jul. 25, 2000, Australian Patent Application No. PQ 9044 filed on Jul. 27, 2000, and Australian Patent Application No. PQ 9045 filed on Jul. 27, 2000, the contents of each being incorporated herein by reference in their entirety.

FIELD OF THE INVENTION

The present invention relates to a method of arthroplasty on a knee joint of a patient. The method extends to both unicondylar knee arthroplasty and knee joint arthroplasty involving resection of both the lateral and medial condyles of the tibia and femur. There is also provided apparatus for use in the method.

BACKGROUND OF THE INVENTION

Various methods and apparatus for performing knee arthroplasty and unicondylar knee arthroplasty in particular, are known in the art. The known methods involve resection of the tibia and femur for fitting of trial tibial and femoral implants, respectively. Once the bone has been resected and the trial implants are secured in place, the surgeon then assesses the kinematics of the knee joint. At this stage, the surgeon may transect, elevate and/or release ligaments and other soft tissue structures to achieve the desired level of deformity correction, balance in the tension of relevant ones of the ligaments and other stabilising soft tissue structures, and an acceptable range of motion of the knee joint. Additional bone resection may also be required to achieve the desired outcome. This leads to an increase in operation time with an associated increase in the risk of surgery related complications. Moreover, such additional surgical intervention following fitting of the trial implants potentially leads to subsequent increased discomfort for the patient and increased healing times. Methods and apparatus for use in arthroplasty of a knee joint are exemplified in U.S. Pat. No. 5,171,244 and U.S. Pat. No. 5,520,695.

SUMMARY OF THE INVENTION

It is an aim of the present invention to ameliorate one or more problems of the prior art or at least provide an alternative to the prior art.

In one aspect of the invention there is provided a method of arthroplasty on a knee joint, comprising the steps of:
  (a) obtaining a desired spacing of the femur from the tibia;
  (b) determining depth of bone to be resected from at least one of the tibia and the femur on the basis of the desired spacing of the femur from the tibia to enable fitting of at least one prosthesis selected from tibial and femoral prostheses;
  (c) resecting bone from one or both of the tibia and the femur substantially to the determined depth in the or each one, respectively; and
  (d) fitting the or each said prosthesis.

The method is particularly suitable for use in unicondylar knee arthroplasty but may also be used in bicondylar knee arthroplasty involving resection of the lateral and medial condyles of both the tibia and the femur. By unicondylar knee arthroplasty is meant arthroplasty involving resection of either the lateral or medial condyles of the tibia and the femur.

The resection of the bone may comprise cutting at least one of the tibia and the femur substantially at the appropriate determined depth in the or each one of the tibia and the femur to remove a segment of bone from the or each one.

Preferably, the resection of the bone from the tibia may comprise forming a recess in the uppermost end of the tibia adjacent to the femur for receiving the tibial prosthesis.

Accordingly, in another aspect of the present invention there is provided a method of arthroplasty on a knee joint, comprising the steps of:
  (a) surgically providing access to the knee joint;
  (b) obtaining a desired spacing of the femur from the tibia;
  (c) determining depth of bone to be resected from an end of the tibia to form a recess for receiving a tibial prosthesis on the basis of the desired spacing of the femur from the tibia;
  (d) resecting the bone from the tibia to the determined depth to form the recess; and
  (e) positioning the tibial prosthesis in the recess.

The method may further comprise locating a guide jig in position about the knee joint for guiding the resection of the bone. Preferably, the guide jig will be adapted for guiding movement of a cutter device relative to the tibia for shaping the recess to a desired profile. Most preferably, the jig will incorporate a template for guiding the movement of the cutter device relative to the tibia.

Preferably, bone will be resected from both the tibia and the femur to enable the fitting of both the tibial and the femoral prostheses.

Preferably, the desired spacing of the femur from the tibia will be obtained using at least one spacer inserted into the knee joint between the femur and the tibia to thereby provide the spacing.

In unicondylar knee arthroplasty only a single spacer will usually be used to obtain the desired spacing of the femur from the tibia. In contrast, in bicondylar knee arthroplasty a pair of spacers will usually be utilised, one being located between each of the lateral and medial condyles of the femur and the tibia, respectively. In this instance, the spacers may have the same thickness or a different thickness to each other.

Most preferably, the or each spacer will be adapted for being positioned between corresponding ones of the condyles of the femur and the tibia.

In another aspect of the present invention there is provided a method of arthroplasty on a knee joint, comprising the steps of:
  (a) surgically providing access to the knee joint;
  (b) selecting at least one spacer for providing desired spacing of the femur from the tibia;
  (c) positioning the selected spacer in the knee joint to obtain the desired spacing of the femur from the tibia;
  (d) using the spacer as a reference to determine a location on each one of the tibia and the femur indicating depth of bone to be resected from each for fitting of chosen tibial and femoral prostheses;
  (e) cutting the tibia and the femur substantially at the determined location on each for resection of the bone from each one to the required said depth; and
  (f) fitting the chosen tibial and the femoral prostheses.

Typically, the knee joint will be placed in a position of flexion whereby the tibia is arranged at an angle with respect to the femur for the resection of the bone. Generally, bone will be resected from a posterior side of the femur and the uppermost end of the tibia.

Preferably, a method of the invention will comprise selecting the at least one spacer from a range of spacers for providing different spacings of the femur from the tibia. Accordingly, the selecting of the or each spacer may comprise;

(i) choosing the spacer from a range of spacers for providing a different spacing of the femur from the tibia, respectively; and (ii) moving the tibia about the femur through an arc of motion between backward and forward positions to evaluate movement of the knee joint while the chosen spacer is in position in the knee joint between the femur and the tibia.

The selecting may further comprise repeating steps (i) and (ii) as necessary to obtain the desired spacing of the femur from the tibia using a different spacer chosen from the range of spacers each time.

The selected spacer will usually be of a thickness for providing appropriate tension and optimising balance in the action of various ligaments and other soft tissue structures of the knee joint during the movement of the tibia about the femur. Preferably, the tension in the knee joint obtained by the spacing of the femur from the tibia with the use of the selected spacer will be substantially retained upon the fitting of the or each prosthesis.

Preferably, the guide jig will be adapted for guiding resection of bone from each of the tibia and the femur. The securing of the guide jig may comprise arranging the jig with the spacer to facilitate the positioning of the jig about the knee joint.

Knowing the relevant dimensions of the chosen tibial and femoral prostheses allows the guide jig to be adapted such that when arranged with the spacer, the guide jig is positioned relative to the tibia and the femur for guiding the cutting of the one or both of them at the depth in the resection of bone therefrom for accommodating the tibial and femoral prostheses. Accordingly, the selected spacer has two roles in unicondylar knee arthroplasty, firstly to space the femur from the tibia and secondly, to act as a reference for resection of bone from one or both of the tibia and the femur to the correct depth.

Therefore, in a further aspect of the invention there is provided a method of determining the position of a guide jig about a knee joint for subsequently guiding resection of one or both of the tibia and the femur to a desired depth in the or each one, respectively, the method comprising:

(a) locating a selected spacer in the knee joint to obtain a desired spacing of the femur from the tibia; and (b) arranging the guide jig and the spacer together to thereby determine the position of the guide jig for guiding the resection of the one or both of the tibia and the femur.

In addition, a combination approach for resecting bone from the femur to the desired depth may be employed. This may involve resecting a segment of bone from the femur to the desired depth in that bone utilising a guide jig as herein described, and inserting an appropriate cutter device into the knee joint between the tibia and the femur in the absence of the guide jig, for resecting bone from the femur with operation of the device and upon movement of the tibia in an arc of motion about the femur to thereby resect further bone from the femur to the desired depth in that bone for fitting of a femoral prosthesis. If desired, only the latter one of those steps may be employed in the resection of the bone from the femur.

Accordingly, in another aspect of the present invention there is provided a method of arthroplasty on a knee joint, comprising the steps of locating a cutter device in position in the knee joint between the tibia and the femur, and moving the tibia through an arc of motion about the femur between backward and forward positions while the cutting device is being operated and is in position between the tibia and the femur, to thereby remove bone substantially to a desired depth from the femur in a direction of travel of the tibia relative to the femur.

There is also provided apparatus for use in the methods of the invention. Apparatus as described herein may be provided in kit form or as an assembled arrangement.

Hence, in a still further aspect of the present invention there is provided apparatus for use in a method of arthroplasty on a knee joint of a patient, comprising:

a guide jig for guiding cutting of at least one of the tibia and the femur in resection of bone therefrom for enabling fitting of one or both of a tibial and a femoral prosthesis, wherein the guide jig is adapted for being arranged with at least one selected spacer for spacing the femur from the tibia, and for being secured about the knee joint in a position determined by the spacer to guide cutting of the at least one of the tibia and the femur substantially at a desired depth in the or each one, respectively.

Typically, the guide jig will be adapted for guiding cutting of the tibia at a fixed predetermined distance below the spacer. Preferably, the guide jig will be adapted for guiding cutting of both the tibia and the femur when the guide jig is secured about the knee joint in said position.

Accordingly, in yet another aspect of the invention there is provided apparatus for use in a method of arthroplasty on a knee joint of a patient, comprising:

a guide jig for guiding cutting of the tibia and the femur in resection of bone therefrom for enabling fitting of chosen tibial and femoral prostheses, and being adapted for being secured about the knee joint in a position determined by at least one spacer for providing a desired spacing of the femur from the tibia, to guide the cutting of the tibia and the femur at a desired depth in each one, respectively.

In still another aspect of the invention there is provided apparatus for use in a method of arthroplasty on a knee joint of a patient, comprising:

(a) at least one spacer having a predetermined thickness for providing a desired spacing of the femur from the tibia; and (b) at least one guide jig for guiding cutting of the tibia and the femur for resection of bone to a desired depth from the or each one respectively, to enable fitting of chosen tibial and femoral prostheses;

wherein the guide jig is adapted for being secured about the knee joint in a position determined by the spacer to guide the cutting of the or each one of tibia and the femur substantially at the desired depth in the or each one.

The spacer will normally be provided as one of a set of spacers for providing different spacings of the femur from the tibia respectively, thereby allowing the selection of different ones of the spacers as needed.

Hence, in yet another aspect of the present invention there is provided apparatus for use in a method of arthroplasty on a knee joint of a patient, comprising;

(a) a set of spacers for allowing selection of at least one said spacer for insertion into the knee joint for providing a desired spacing of the femur from the tibia; and (b) at least one guide jig for guiding cutting of one or both of the tibia and the femur for resection of bone to a desired depth from the or each one respectively, to enable fitting of chosen tibial and femoral prostheses;

wherein the guide jig is adapted for being secured about the knee joint in a position determined by the spacer to guide the cutting of the one or both of tibia and the femur substantially at the desired said depth in the or each one, and wherein the spacers have a different thickness to one another for providing different spacings of the femur from the tibia.

The guide jig may be adapted for guiding the cutting of the femur and the tibia at the same depth in each one or at a different depth in the tibia compared to the femur.

Preferably, the guide jig will be adapted for guiding the cutting of the tibia and the femur at a predetermined fixed spacing. The guide jig will normally be adapted for being coupled with one or more said spacers. The term "coupled" is to be taken in the broadest sense and includes within its scope reception of the spacer(s) by the jig whether the or each spacer is fixed to the guide jig or not.

Preferably, the guide jig will comprise a cutting block adapted for receiving the or each selected spacer and most preferably, will have a through passageway for guiding the cutting of one of the condyles of tibia and the femur. More preferably, the guide jig will have another through passageway for guiding the cutting of the other of the condyles. Most preferably, the cutting block will be adapted for being secured to the tibia.

Generally, the guide jig will be adapted for guiding cutting of one or both of the tibia and the femur in a medial to lateral or lateral to medial direction with respect to the knee joint.

Preferably, the guide jig will be adapted for being secured about the knee joint in a position determined by the thickness of the spacer or spacers used.

In another aspect of the present invention there is provided a spacer for being inserted into a knee joint for spacing the femur from the tibia, comprising an elongate member with a leading end region adapted for being positioned between the tibia and the femur to space the femur from the tibia, and an opposite end region for protruding from the knee joint.

In a further aspect of the present invention there is provided a spacer for being inserted into a knee joint to provide a desired spacing of the femur from the tibia in arthroplasty on the knee joint, comprising an elongate member with a leading end region adapted for being inserted between the tibia and the femur to thereby obtain the desired spacing of the femur from the tibia and being retained in the knee joint during resection of bone to a desired depth from one or both of the tibia and the femur respectively, and an opposite end region adapted for protruding from the knee joint and coupling with a guide jig for guiding the cutting of the or each one of the tibia and the femur in the resection of the bone.

Preferably, the leading end region of the spacer will be adapted for retaining the spacer in the knee joint. Most preferably, the leading end region of the spacer will be adapted for receiving the medial or lateral condyle of the femur for retaining the spacer in the knee joint.

In yet another aspect of the present invention there is provided a set of spacers for allowing selection of at least one of the spacers for insertion into a knee joint to provide a desired spacing of the femur from the tibia in arthroplasty on the knee joint, each said spacer respectively comprising an elongate member with a leading end region adapted for being inserted between the tibia and the femur to thereby space the femur from the tibia and being retained in the knee joint during resection of bone from one or both of the tibia and the femur respectively, and an opposite end region adapted for protruding from the knee joint and coupling with a guide jig for guiding cutting of the or each one of the tibia and the femur in the resection of the bone, wherein the spacers have a different thickness to one another for providing different spacings of the femur from the tibia.

Usually, it is desirably to resect the tibia at an angle sloping downwardly in the anterior to posterior direction of the knee joint for location of the tibial prosthesis on the resulting sloping surface of the tibia. Typically, the angle of slope is about 3° although this may vary from patient to patient.

Accordingly, in another aspect of the present invention there is provided an alignment device for aligning a guide jig in position about a knee joint for guiding cutting of at least one of the tibia and the femur at a desired location on the or each one respectively during arthroplasty on the knee joint, and comprising:

a body for receiving the guide jig and coupling the guide jig with an alignment guide for aligning the guide jig in a desired medial to lateral orientation with respect to the knee joint;

and wherein the body is adapted for aligning the guide jig at a desired angle in an anterior to posterior direction of the knee joint for securing of the guide jig at the desired angle prior to removal of the body from about the knee joint for allowing cutting of the one or both of tibia and the femur to be guided by the guide jig.

In still another aspect of the present invention there is provided an alignment device for supporting a cutting device for resecting bone from the tibia to a desired depth to from a recess in the tibia during arthroplasty on a knee joint, and comprising:

a body for receiving a guide jig for guiding cutting of the femur and coupling the guide jig with an alignment guide for aligning the guide jig in a desired medial to lateral orientation with respect to the knee joint;

and wherein the body is adapted for aligning the guide jig at a desired angle in an anterior to posterior direction of the knee joint and for being secured about the knee joint in a position determined by the guide jig for supporting the cutting device for the resection of the bone from the tibia following removal of the guide jig from the body.

Accordingly, there is also provided an alignment guide for supporting the guide jig and aligning the guide jig in a desired medial to lateral orientation with respect to the knee joint to allow for varus and valgus adjustment.

The alignment guide will typically incorporate a mounting platform which is angularly displaceable for allowing orientation of the guide jig in the medial to lateral direction. Desirably, the mounting platform will be adapted for supporting the guide jig adjacent to the medial condyles of the tibia and femur or the lateral condyles of the bones as may be required. The alignment guide will generally be a tibial alignment guide for being secured along the leg of the patient in alignment with the tibia.

Alternatively, the guide jig itself may be adapted for guiding the cutting of one or both of the tibia and the femur at the desired angle in the medial to lateral direction of the knee joint. Similarly, the guide jig may be adapted for guiding cutting of the one or both of the tibia and femur at the downward angle in the anterior to posterior direction of the knee joint, in which case the alignment component described above for this purpose may not be utilised and the cutting block may be mounted directly on the alignment guide.

In still another aspect there is provided the use of a guide jig of the invention in the assembly of a medical device for arthroplasty of the knee, wherein the medical device comprises the guide jig and at least one spacer for spacing the femur from the tibia.

In still another aspect there is provided the use of at least one spacer of the invention in the assembly of a medical device for guiding resection of bone from at least one of the tibia and the femur in arthroplasty of the knee.

In a further aspect there is provided the use of at least one spacer of the invention in the assembly of a medical device for knee arthroplasty, wherein the medical device comprises the or each spacer and a guide jig of the present invention.

Advantageously, the method of the invention may allow balancing of tension in ligaments and other soft tissue structures of the knee joint to be optimised prior to resection of bone for the fitting of the prostheses. Moreover, ligament and soft tissue release to obtain adequate balancing of tension in the ligaments and soft tissue of the knee joint during flexion and extension of the knee joint as is required for optimum knee joint kinematics prior to or following fitting of trial tibial and femoral implants may be eliminated or reduced.

In addition, the risk of incorrect alignment and orientation of the tibial and femoral prostheses relative to one another with reference to the action of the ligaments and soft tissue structures may be reduced.

It is another advantage that as the use of a spacer or spacers as herein described may facilitate both positioning of the guide jig and appropriate tensioning of ligaments and other soft tissue structures of the knee joint, decreased operating times may be provided thereby potentially reducing the incidence of various time related surgical complications such as wound infection, complications associated with the risk of anaesthetic, and thrombosis associated with tourniquet application which can lead to pulmonary embolus and other serious problems. Furthermore, by reducing the need to transect, elevate, or release ligaments and other soft tissue structures of the knee joint, post-operative recovery time may be reduced with consequential reductions in overall health care costs associated with knee arthroplasty.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

The features and advantages of the present invention will become further apparent from the following detailed description of a number of preferred embodiments illustrated in the accompanying drawings.

BRIEF DESCRIPTION OF THE ACCOMPANYING DRAWINGS

FIG. 10(a) is a rear perspective view of a guide jig of the apparatus shown in FIG. 8;

FIG. 10(b) is a side view of the guide jig of FIG. 10(a);

FIG. 11 is a view of an alignment component of the apparatus shown in FIG. 8.

Figure 8:
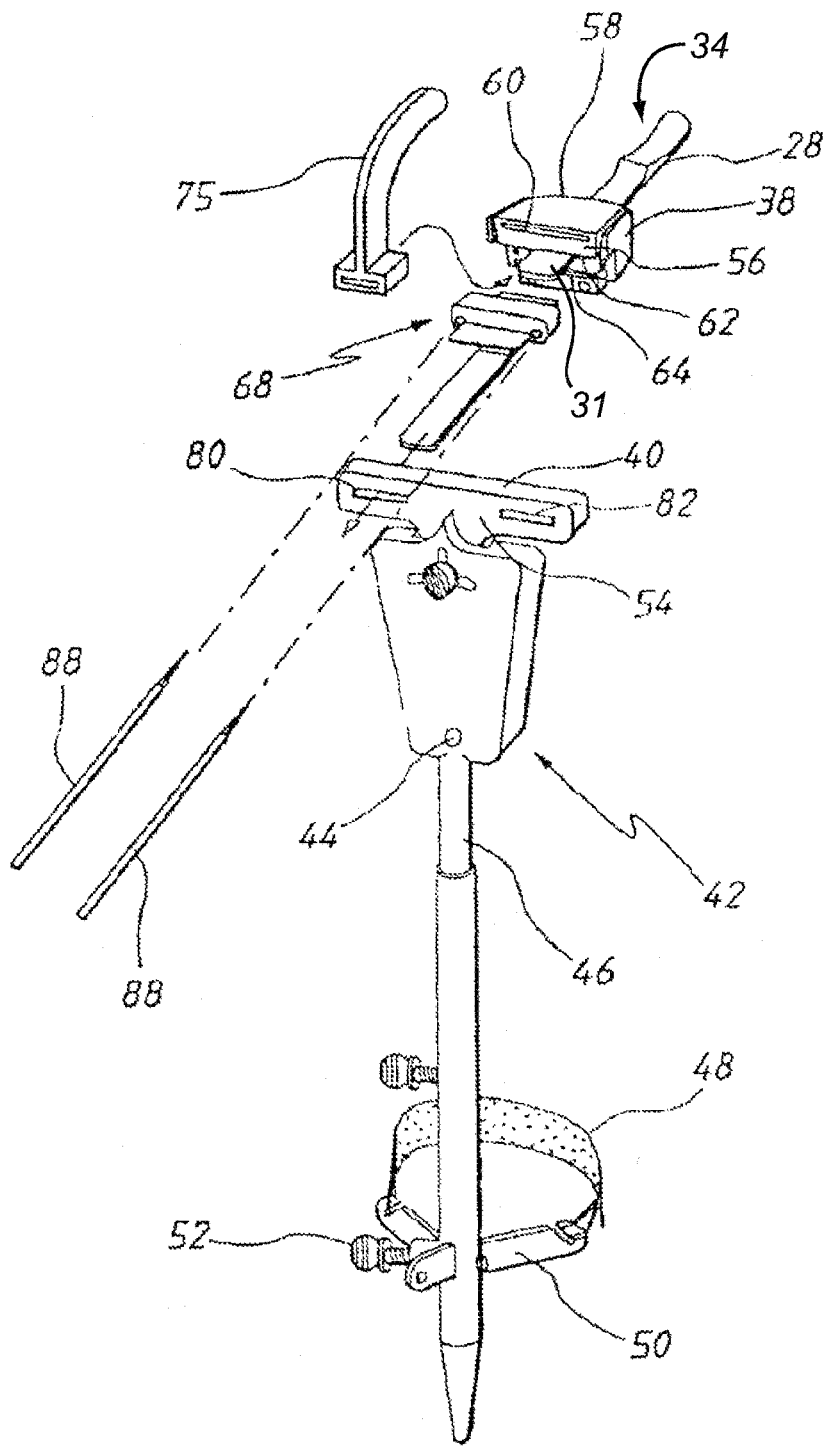
FIG. 8 is a perspective exploded view of apparatus for performing arthroplasty on a knee joint.
Figure 33A:
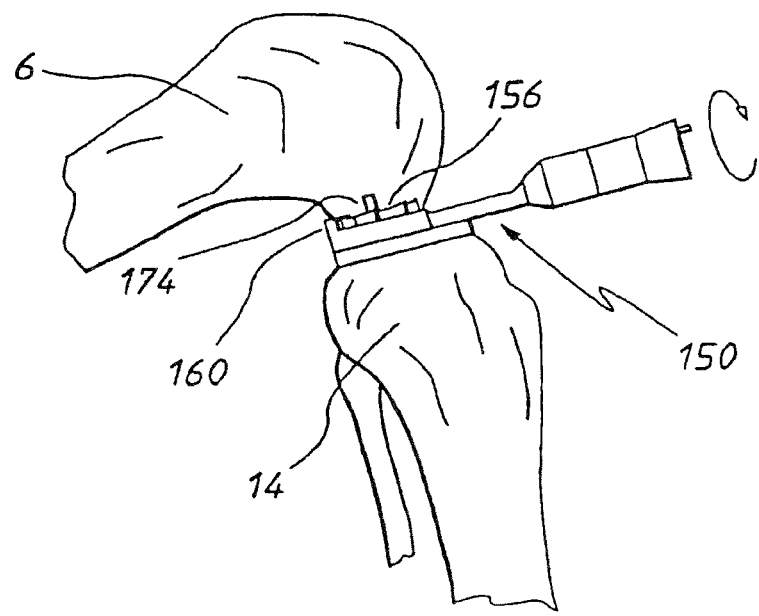
Figure 33B:
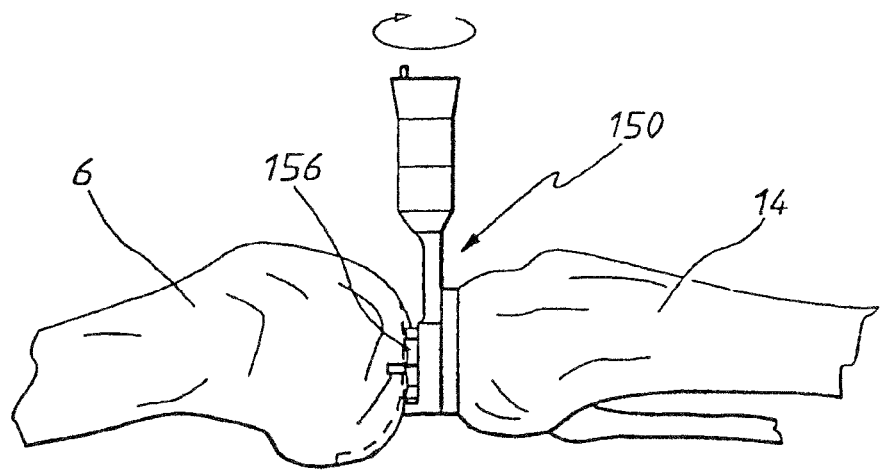
Figure 33C:
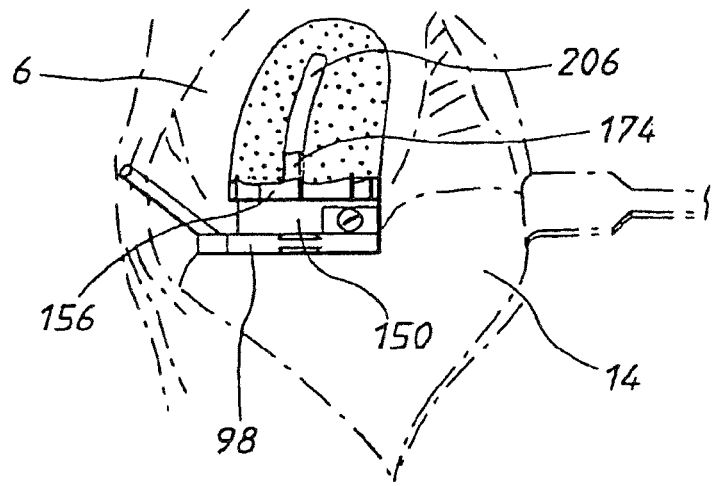
Figure 34:
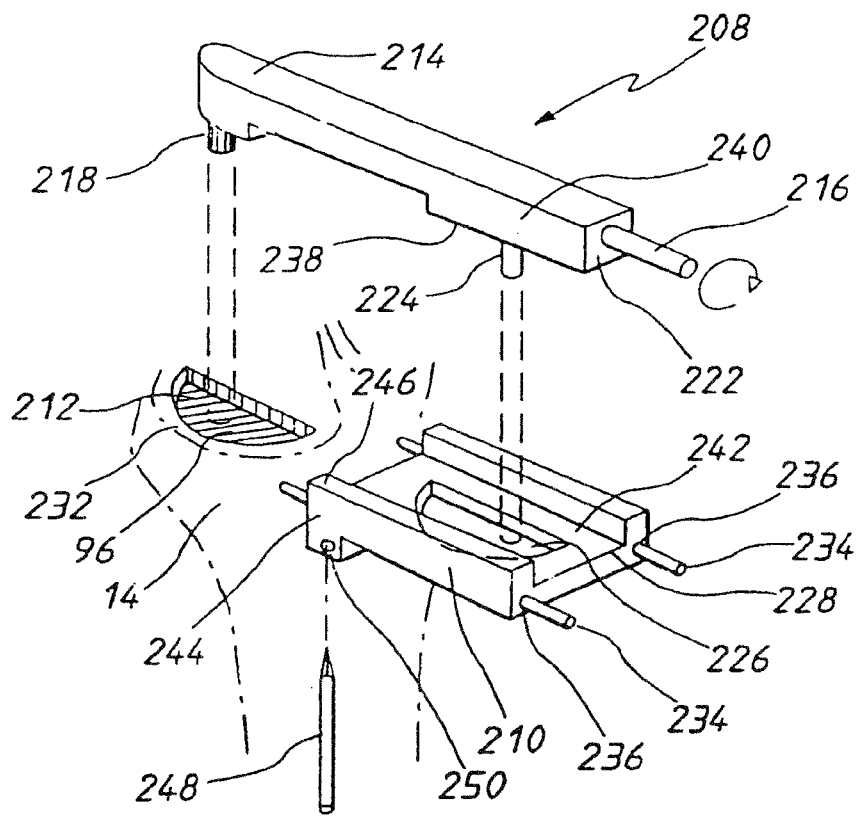
Figure 35:
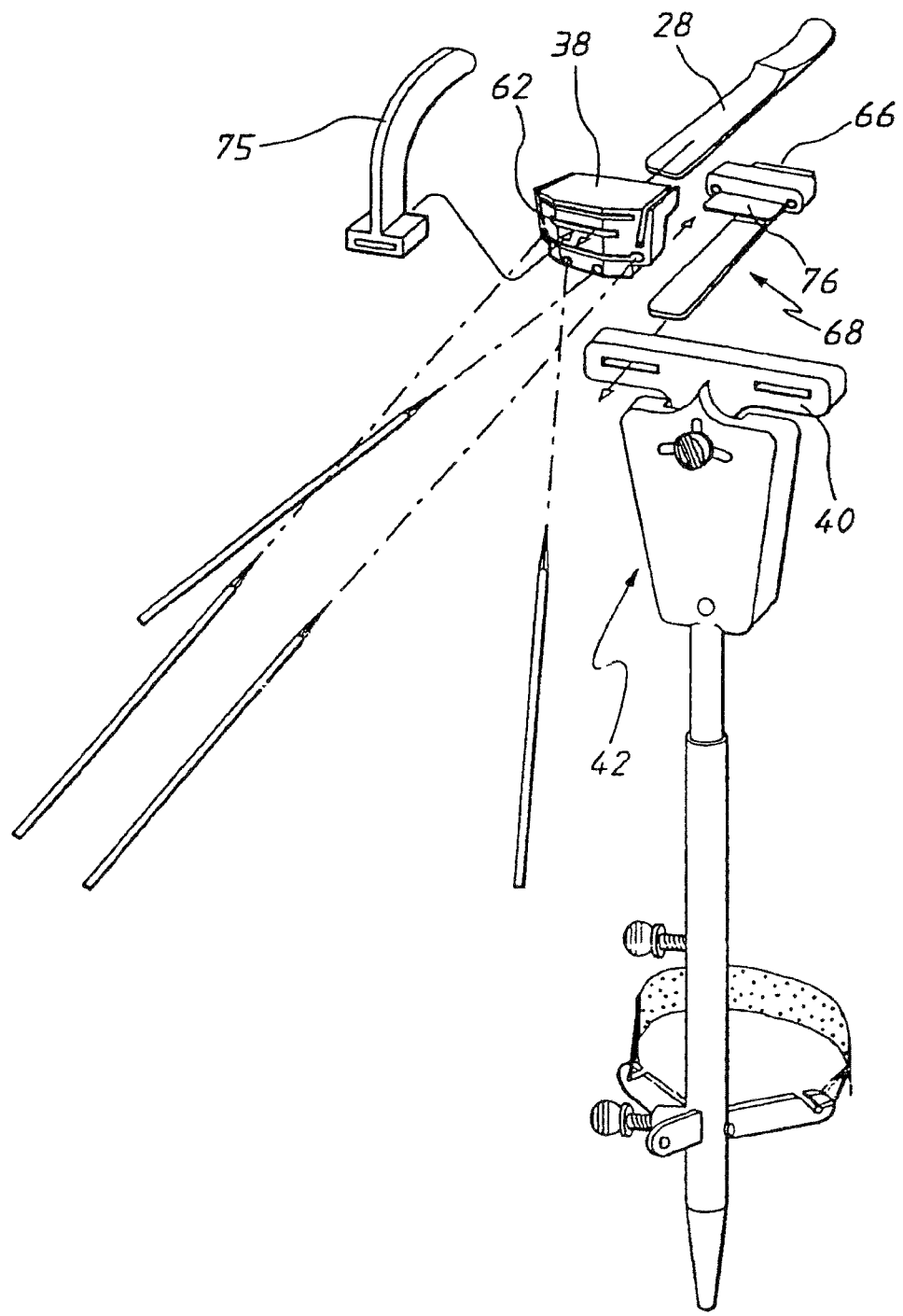
Figure 36:
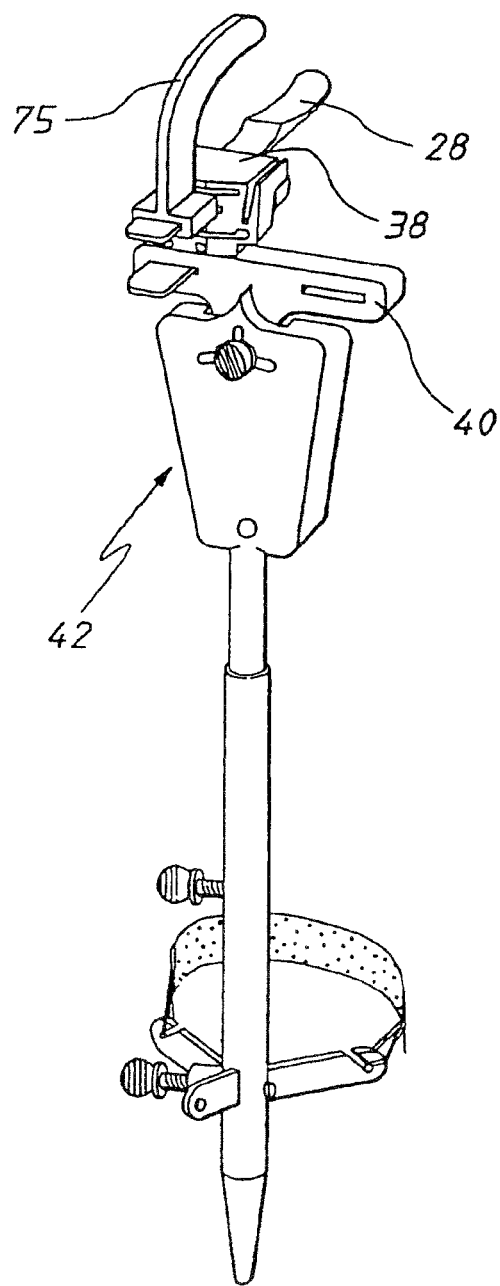
Figure 37:
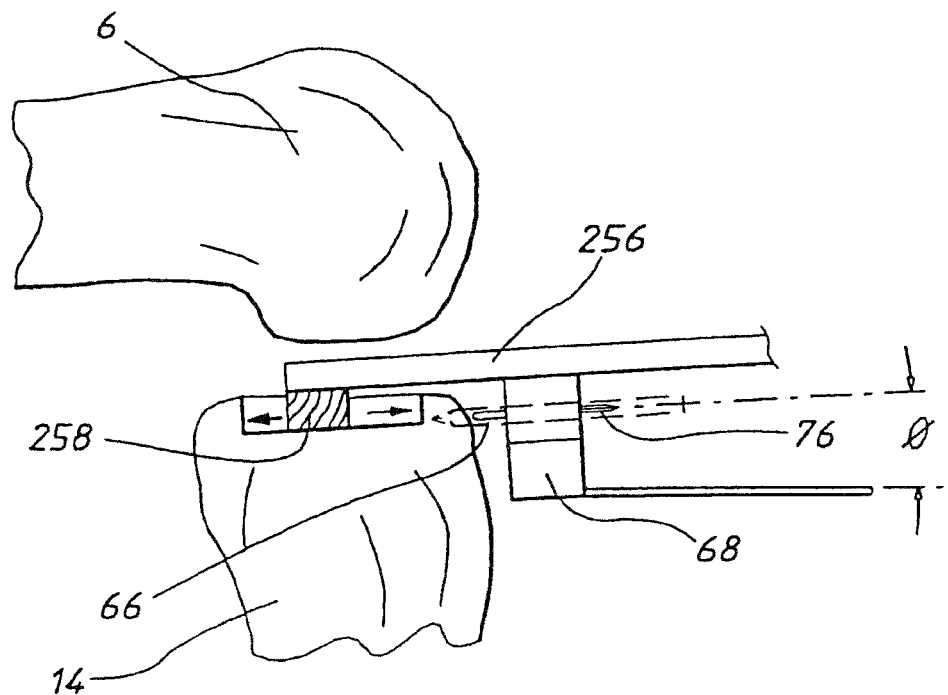
Figure 38:
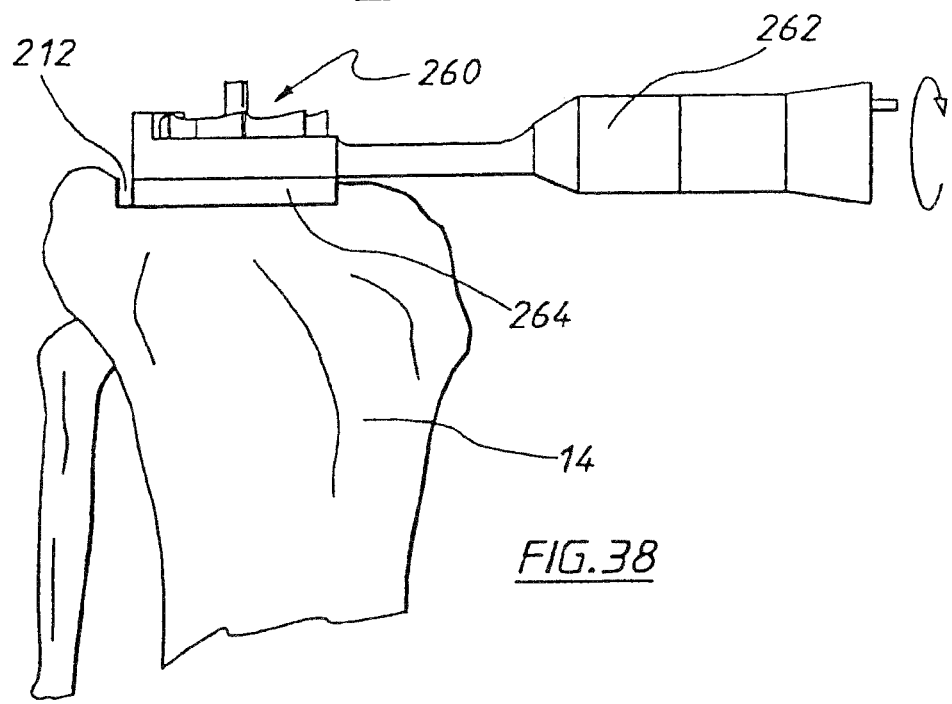

FIGS. 33(a) to 33(c) illustrate the resection of bone to a desired depth from the femur;

FIG. 34 is an exploded perspective view of an assembly for forming a recess in the tibia for receiving a tibial implant;

FIG. 35 is an exploded perspective view of the apparatus of FIG. 8 when arranged for removal of bone from the tibia for inset placement of a tibial implant;

FIG. 36 is a perspective view of the apparatus arranged as shown in FIG. 35 when assembled;

FIG. 37 illustrates removal of bone from the tibia for inset tibial implant placement utilising apparatus of the invention; and FIG. 38 illustrates a further cutting device for resecting bone to a desired depth from the femur.

DETAILED DESCRIPTION OF PREFERRED EMBODIMENTS OF THE PRESENT INVENTION

Figure 1:
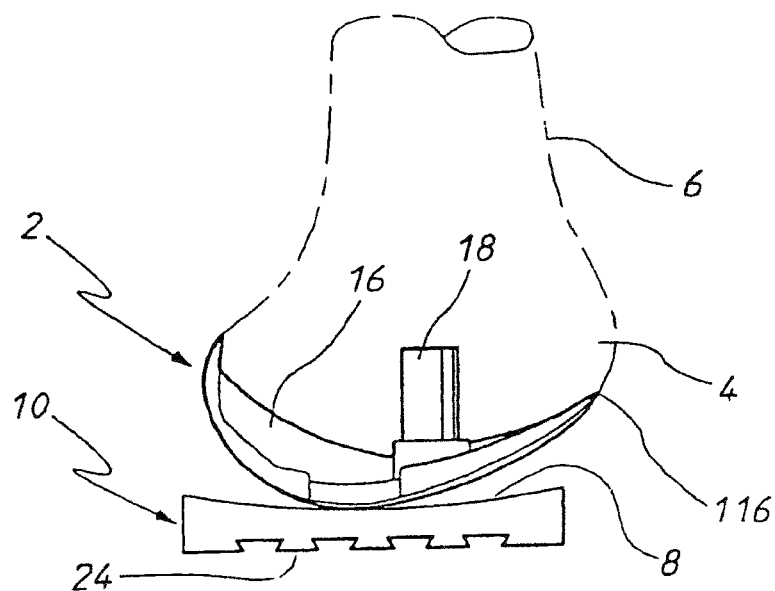
FIG. 1 is a side schematic view illustrating a knee joint with tibial and femoral prostheses fitted.
Figure 2:
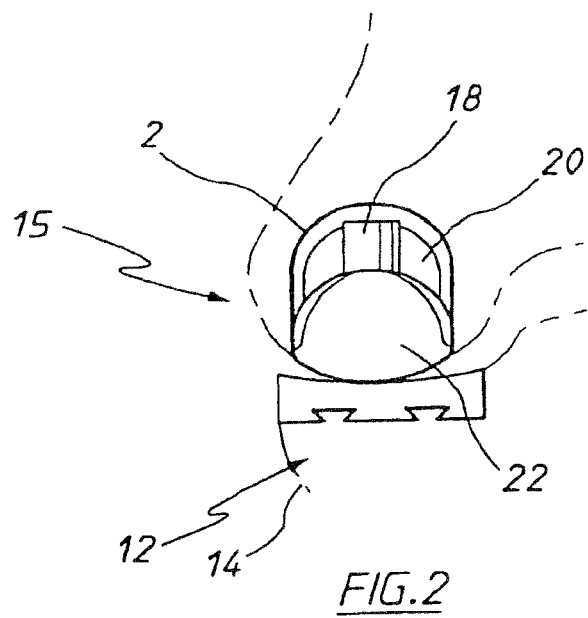
FIG. 2 is an anterior view of the fitted tibial and femoral prostheses shown in FIG. 1.

The femoral prosthesis 2 shown in FIG. 1 is fitted to the medial condyle 4 of the femur 6 and abuts articulating surface 8 of the tibial prosthesis 10 fitted on the corresponding medial condyle 12 of the tibia 14, for articulation thereon as the tibia undergoes flexion and extension about the knee joint 15. The positioning of the femoral prosthesis 2 and the tibial prosthesis 10 is more clearly shown in FIG. 2.

Figure 3:
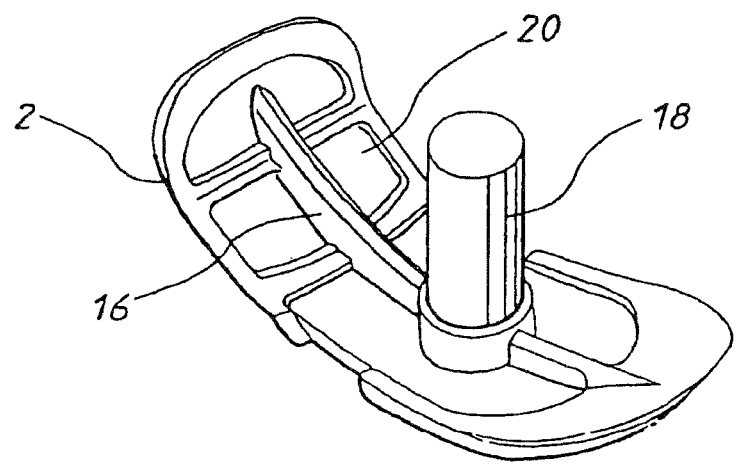
FIG. 3 is a perspective view of the femoral prostheses shown in FIG. 1 prior to being fitted.

As shown in FIG. 3, the femoral prosthesis 2 is provided with a centrally orientated upstanding fin 16 incorporating a peg 18 projecting from an interior face 20 of the prosthesis.

The opposite outer face 22 has a curved contour for facilitating movement of the tibia about the femur. The interior face 20 of the femoral prosthesis is textured to enhance binding of bonding cement used to fix the prosthesis to the femur. The prosthesis itself is formed from a cast cobalt chromium molybdenum alloy conventionally used in the manufacture of such prostheses.

Figure 4:
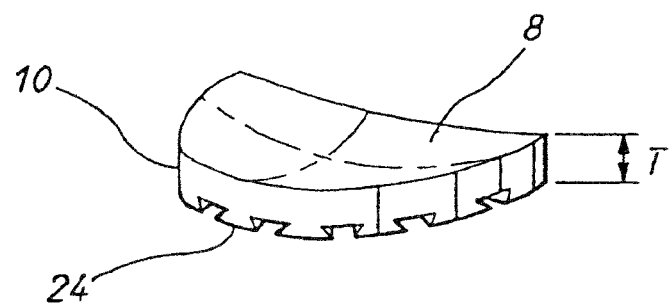
FIG. 4 is a perspective view of the tibial prostheses shown in FIG. 1 prior to being fitted.

The tibial prosthesis 10 shown more clearly in FIG. 4 is manufactured from ultra high molecular weight polyethylene and has a dove tailed base 24 to again enhance bonding of cement to the prosthesis for fixing the prosthesis to the tibia. The articulating surface 8 of the tibial prosthesis is sightly concaved to substantially match curvature of the outer face 22 of the femoral prosthesis.

Figure 5:
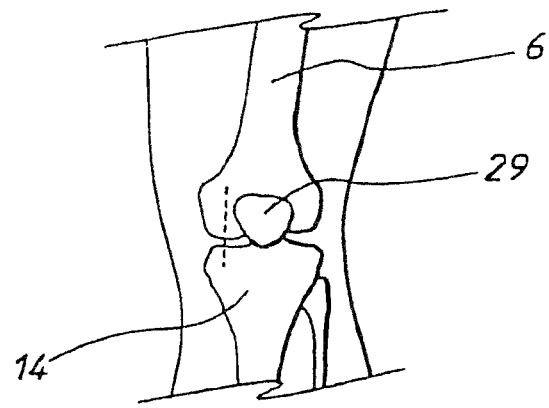
FIG. 5 is a diagrammatic front view of a knee joint.

An example of unicondylar arthroplasty will now be described. As a first step, a longitudinal incision is made in the knee from just medial to the medial edge of the patella 26 to just below the medial tibial plateau adjacent to the attachment of the iliotibial tract, as indicated by the dotted line in FIG. 5. The incision avoids transecting any of the ligamentous structures that contribute to the kinematics of the knee. The patella is not everted, but gently retracted laterally to expose the medial compartment of the knee. All femoral and tibial osteophytes which are accessible are then removed.

Figure 6:
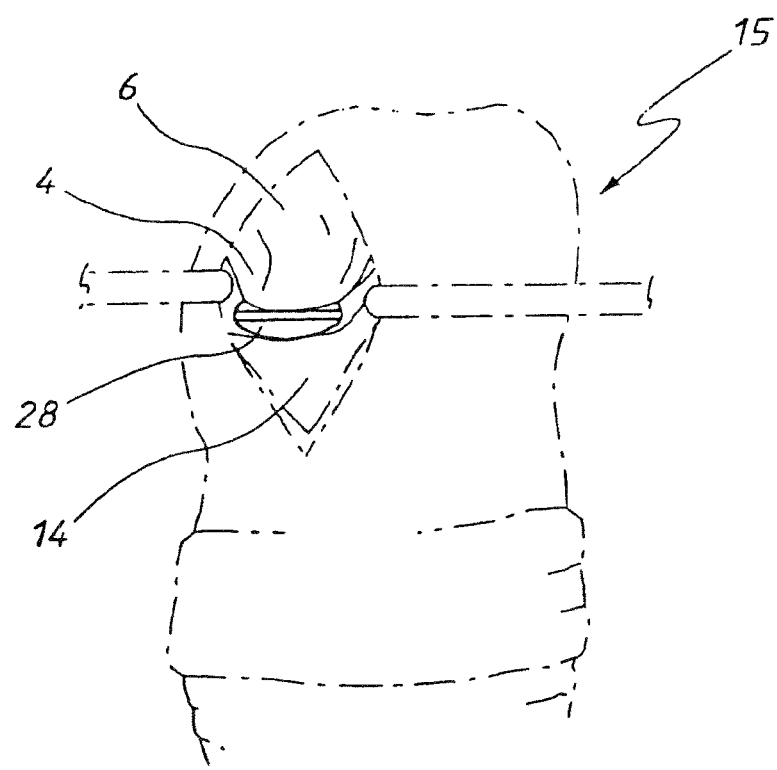
FIG. 6 is a diagrammatic front view showing a spacer in position between a femur and a tibia of the knee joint illustrated in FIG. 5.

In order to balance tension in ligaments and other soft tissue structures of the knee joint as well as to correct deformity, a spacer 28 is located in position between the condyle of the femur and the corresponding condyle of the tibia as shown in FIG. 6. The spacer effectively spaces the femur from the tibia.

To check for adequate tension of the soft tissue structures and kinematics of the knee joint, the tibia is moved through an arc of flexion of between 0° to about 130°. If the knee joint is unstable or has inadequate tension, the spacer may be removed and a spacer having a greater thickness for spacing the tibia and the femur further apart may be located in the joint. Conversely, if the knee feels over tensioned or adequate range of movement through the arc of flexion cannot be achieved, the spacer may be replaced with a spacer having a reduced thickness to decrease the spacing between the femur and the tibia. This process may be repeated a number of times using a spacer having a different thickness each time until adequate tension and kinematics of the knee joint is achieved.

Importantly, the method enables the tensioning of soft tissue structures in the knee joint to be optimised prior to any bone being resected from the tibia or the femur in preparation for fitting of the tibial and femoral prostheses. Moreover, the tensioning may be obtained without the need to transect, elevate or release soft tissue structures of the knee joint. However, further adjustment of the tensioning in the knee joint as may be deemed necessary using such procedures is not excluded.

Figure 7:
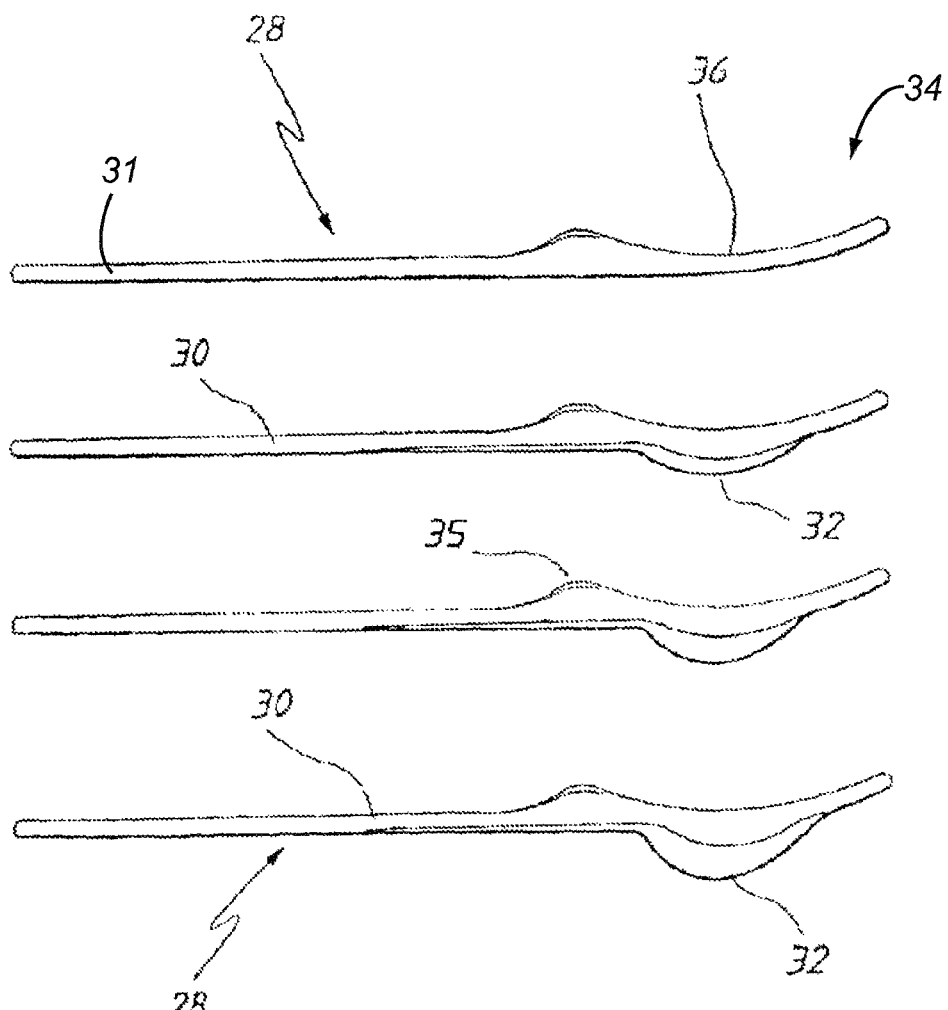
FIG. 7 is a diagrammatic side view of a set of different spacers, for providing different spacing of the femur from the tibia.

A set of spacers from which the appropriate spacer 28 may be selected is illustrated in FIG. 7. The spacers each comprise an elongate body 30 for being inserted into the knee joint between opposing condyles of the tibia and the femur. The body 30 has a bulbous protrusion 32 formed on an underside of a leading end region 34 thereof for being seated on the sulcus of the relevant tibial condyle. As can be seen, the leading end region of each spacer is scooped upwardly forward of transverse ridge 35 thereby defining a trough 36 for receiving the condyle of the femur. The scooped contour of the leading end region of the spacer facilitates insertion of the spacer into the knee joint and assists in retaining the spacer in position once located in the knee joint.

As will be appreciated, the spacing of the femur from the tibia is determined by the thickness of the bulbous protrusion. In the spacer set shown, the thickness of the respective spacers increases in 1 mm increments. However, sets of spacers having a different thickness range may of course be used instead.

Once the appropriate spacer 28 has been selected and located in position in the knee joint, apparatus as shown in FIG. 8 for guiding cutting of the tibia and the femur for resection of bone therefrom is secured in position about the knee joint. The apparatus comprises a guide jig in the form of a tibiofemoral cutting block 38 adapted for being securely mounted on mounting platform 40 of tibial alignment guide 42.

Tibial alignment guide 42 is adapted for being aligned along the longitudinal axis of the tibia and the mounting platform 40 is able to be angularly adjusted relative thereto about pivot 44 to accommodate required varus or valgus adjustment in the medial to lateral direction of the knee joint as may be necessary. Angular displacement of the mounting platform is achieved by loosening lock nut 52 and rotating the platform about the pivot pin 44 to the desired angle with reference to a scale (not shown) marked on the front face 54 of the tibial alignment guide, and subsequently retightening the lock nut 52. Shaft 46 of the alignment guide is telescopic to permit an ankle strap 48 carried on the bracket 50 mounted on the lower end region of the alignment guide to be secured around the ankle.

A more detailed view of the cutting block 38 is shown in FIG. 10(a). As indicated, a number of slots extending through the cutting block from a front face 56 to an opposite rear face indicated by the numeral 58 are defined in the cutting block. In particular, the cutting block incorporates an upper slot 60 for guiding cutting of the femur in the resection of bone therefrom, and a middle slot 62 for receiving the protruding end region of the spacer when inserted in the knee joint. A lower slot 64 is also defined in the cutting block for reception of rear tongue 66 of alignment component 68. The distance between the top 70 of the slot 62 and the bottom 72 of the lower slot 64 corresponds essentially to the thickness T of the tibial prosthesis 10 of FIG. 4. A pair of inwardly directed channels 73(a) and 73(b) are also defined in opposite side regions of the cutting block, one in each side region respectively, for guiding downwardly directed cuts into the tibia in the resection of bone therefrom. A side view of the cutting block 38 is shown in FIG. 10(b).

Figure 9A:
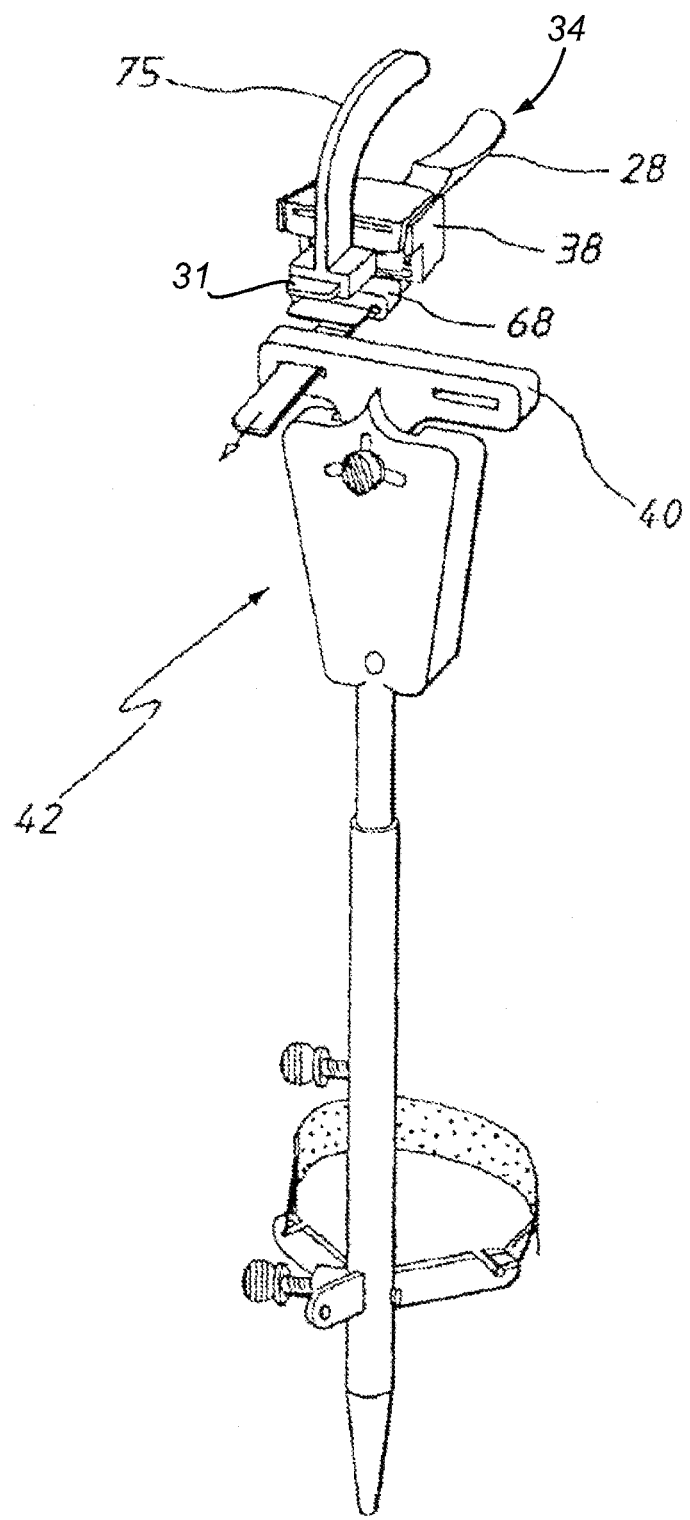
FIG. 9(a) is a perspective view of the apparatus of FIG. 8 when assembled.
Figure 9B:
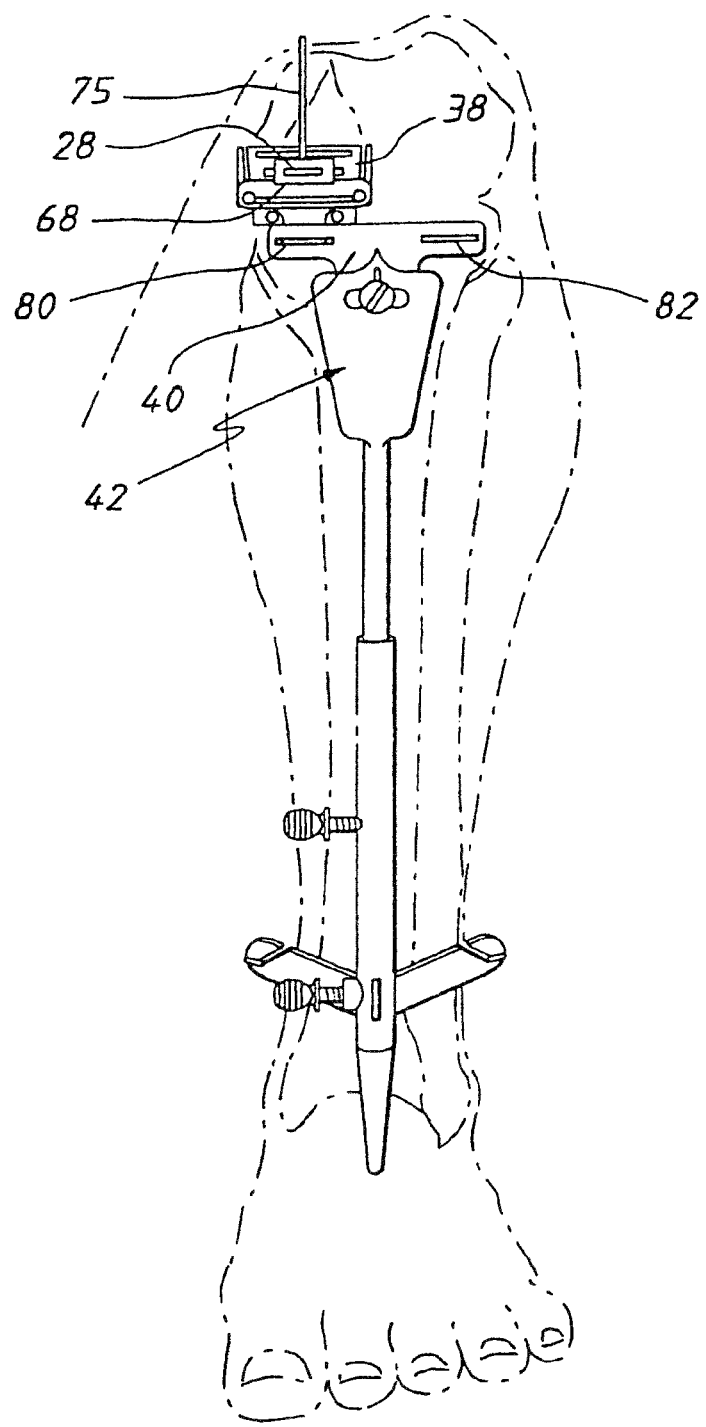
FIG. 9(b) is a diagrammatic front view of the apparatus of FIG. 8 fitted to the leg of a patient.

The apparatus when assembled is shown in FIG. 9(a) and when secured in position about the knee joint in FIG. 9(b). As can be seen, the apparatus further incorporates a stylus 75 for assisting alignment of the cutting block with the femur and which is mounted on the protruding end of the spacer 28.

As shown in FIG. 11, the alignment component consists of a body 74 incorporating a forwardly projecting tongue 76 which lies in the same plane as rearwardly projecting tongue 66 and overlies a long tongue 78 of the body provided for insertion into slot 80 or 82 of the mounting platform 40 of the tibial alignment guide 42. The plane in which the forward and rearward tongues 76 and 66 lie extends at an angle ϕ relative to the long tongue 78 such that tongue 76 diverges from the long tongue 78 with distance along the long tongue.

Accordingly, the cutting block 38 when mounted on the alignment component and assembled with the tibial alignment guide 42 is orientated for guiding resection of bone at a downward angle of ϕ in the anterior to posterior direction of the knee joint. Typically, angle ϕ will be 3° although different alignment components may be provided in which angle ϕ differs from one to the next to allow selection of the most appropriate one for each patient. Alternatively, an alignment component may be utilised in which the tongues 66 and 76 lie substantially parallel with the long tongue 78 in the case where it is desirable for the tibia to be cut in a substantially horizontal plane of the tibia.

As will be appreciated, the slots 80 and 82 of the mounting platform 40 of the tibial alignment guide are spaced apart from each other along the mounting platform for allowing the cutting block 38 to be positioned adjacent to the lateral and medial condyles of either the right or left tibiae, respectively.

Once the cutting block is secured to the tibia as will be described further below, the alignment component 68 and the tibial alignment guide 42 are removed from about the knee joint without disturbing the cutting block and spacer assembly. This leaves lower guide slot 72 of the cutting block vacant for reception of a saw and subsequently guiding cutting of the medial condyle of the tibia in the resection of bone for fitting of the tibial prosthesis. The resection of bone from the tibia and the femur is performed while the knee is placed in about 90° to about 100° of flexion.

In this position, the top slot 60 of the cutting block 38 guides the saw for cutting of a posterior chamfer from the femoral condyle for fitting of the femoral prosthesis and as such, both the tibia and the femur are cut in a plane extending in the medial to lateral direction, respectively.

Figure 12:
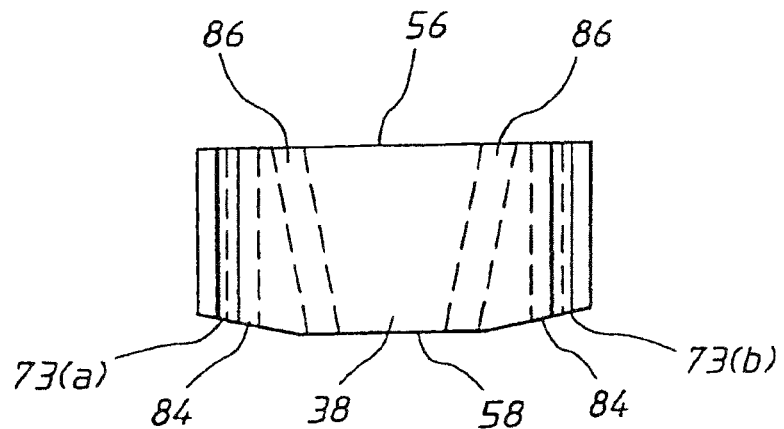
FIG. 12 is a schematic plan view of the guide jig of FIG. 10 indicating the orientation of channels defined in the jig for reception of pins for securing the jig in position about the knee joint.

Channels 84 and 86 are provided in the cutting block for reception of trocar pins 88 for securing the cutting block to the tibia. As shown schematically in FIG. 12, the bottom channels 86 converge toward each other in the front to the rear direction of the cutting block and are obliquely orientated with respect to the top pair of channels 84. Apertures 90 defined in the alignment component 68 are positioned to align with channels 84 of the cutting block when the cutting block is mounted on the tibial alignment guide to thereby hold the cutting block and alignment component together upon trocar pins being inserted therethrough into the tibia. In this way, the alignment component can be slid off the free end of the trocar pins leaving the cutting block behind in position about the knee joint.

Figure 13:
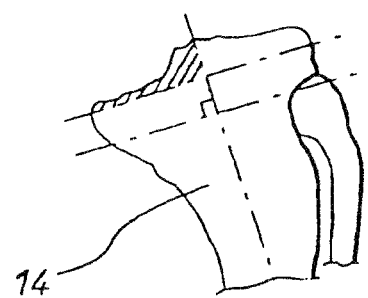
FIG. 13 is a diagrammatic partial view of a tibial shaft.

In the case of bowed varus tibiae, the cutting block will be arranged substantially perpendicular with respect to the metaphyseal axis of the tibial shaft as indicated in FIG. 13.

Figure 14:
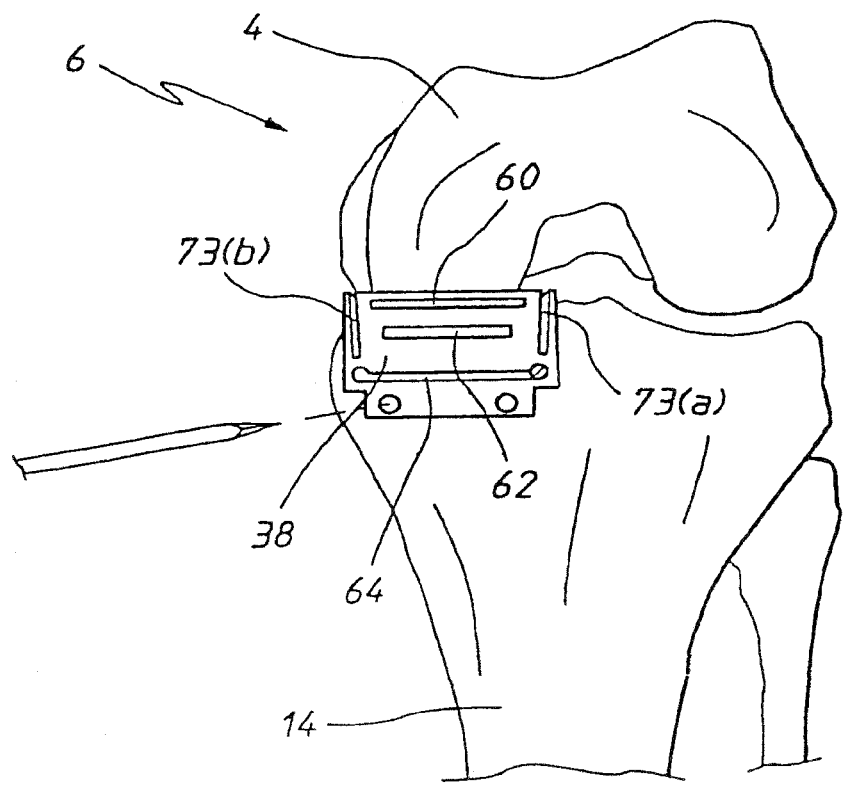
FIG. 14 is a diagrammatic front view of the guide jig fitted in position about the knee joint.
Figure 15:
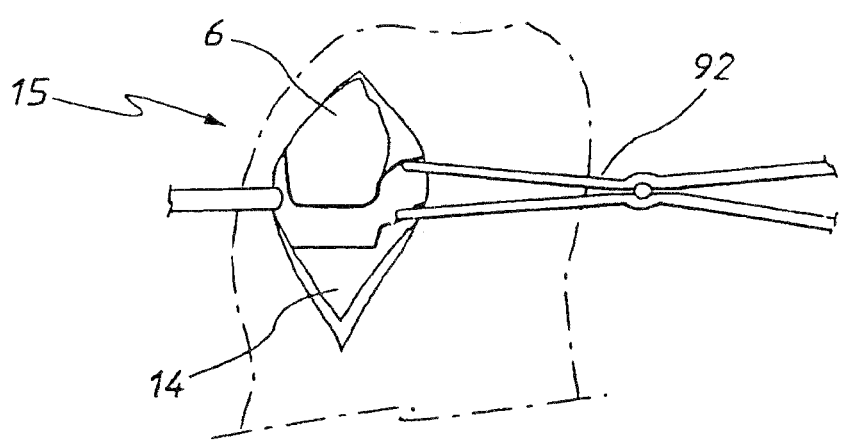
FIG. 15 is a front diagrammatic view showing the medial condyles of the femur and the tibia following resection thereof.

FIG. 14 illustrates the positioning of the cutting block 38 for the resection of the medial condyles of the tibia and femur while the tibia is placed in flexion with respect to the femur, and with the alignment component 68 and tibial alignment guide 42 removed. Once the transverse cuts to the tibia and the femur have been performed, a downwardly directed cut into the tibia guided by the relevant one of channel 73(*a*) or 73(*b*) of the cutting block is performed for removal of a segment of bone from the tibia to form a recess therein. The cutting block 38 and spacer 28 assembly is then removed to allow the downwardly directed cut into the tibia to be completed. At this time, any remaining posterior osteophytes and meniscus are also removed as required. The resected medial condyles of the tibia and femur following removal of the cutting block and spacer assembly is shown in FIG. 15. The use of a knee joint spreader 92 to maintain suitable access to the knee joint space is also shown. Alternatively, a suitable retractor may be utilised.

Figure 16:
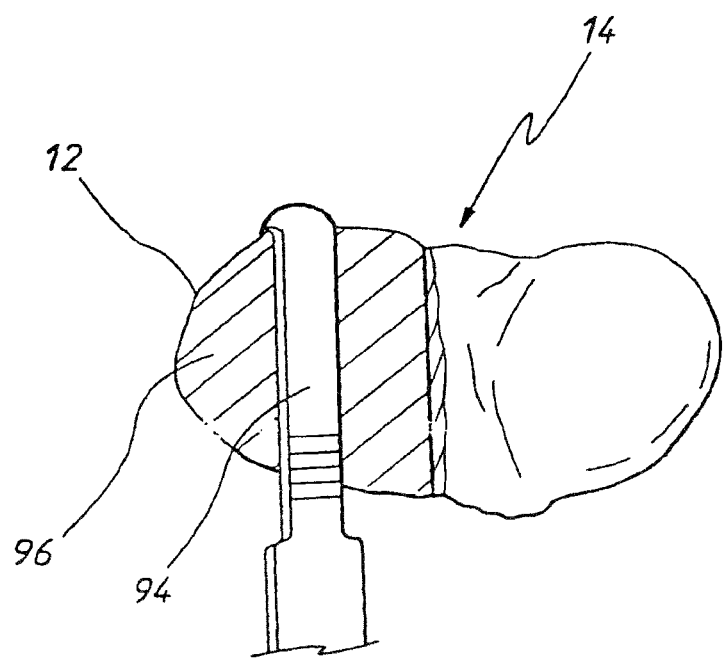
FIG. 16 is a diagrammatic view illustrating the use of a tibial sizing device for determination of an appropriate size of tibial implant.
Figure 17:
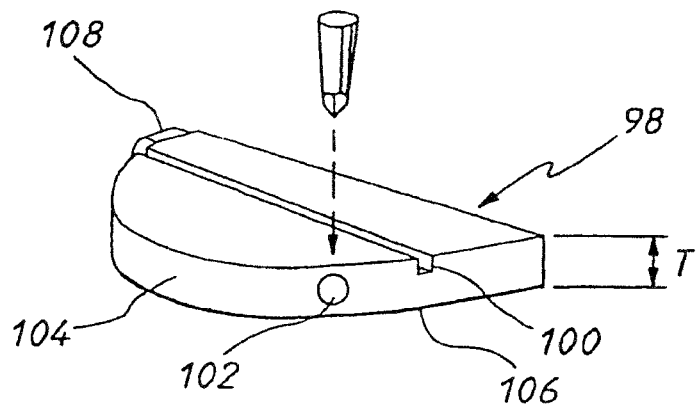
FIG. 17 is a perspective view of a tibial trial.

A diagrammatic plan view of the resected tibia is shown in FIG. 16. As indicated, following resection of the tibia, a tibial sizing device 94 is used to check the anteroposterior dimension of the resected tibial surface 96 for selection of an appropriately sized tibial trial 98 for being pinned into position on the resected surface. An example of a suitable tibial trial is illustrated in FIG. 17.

The profile of the tibial trial 98 and its thickness T match that of the tibial prosthesis 10. As will be appreciated, and with reference to FIG. 16, the profile of both the tibial trial 98 and tibial prosthesis 10 substantially match the profile of the resected tibial surface 96 of the tibia.

Figure 18:
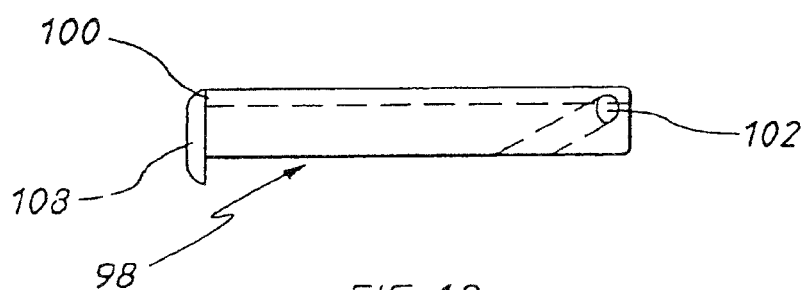
FIG. 18 is a diagrammatic view of the tibial trial of FIG. 17.

A channel in the form of a guide groove 100 is defined across the tibial trial for being orientated in the anteroposterior direction when the tibial trial is fitted in position. An obliquely orientated channel 102 extends from the side face 104 of the tibial trial through to its base 106 for reception of a pin therein for securing the tibial trial to the tibia. A tab 108 on the posterior side of the tibial trial depends from the base 106 as is more clearly shown in the diagrammatic size view of the tibial trial shown in FIG. 18, for assisting positioning of the tibial trial on the resected surface of the tibia.

Figure 19:
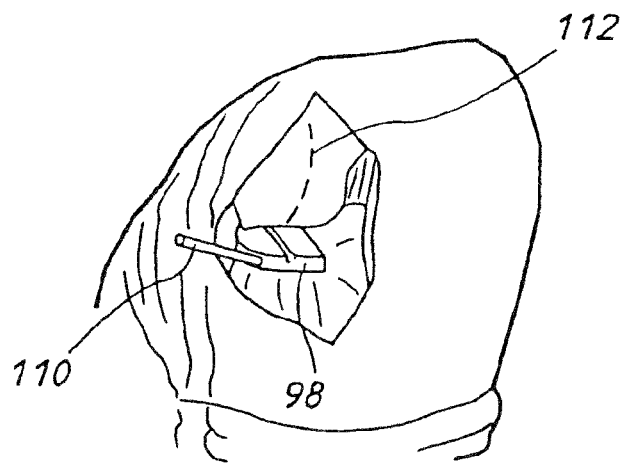
FIG. 19 is a diagrammatic anterior view of the tibial implant of FIG. 16 fixed in position on the tibia of the knee joint.

The tibial trial when secured in position on the resected tibial surface 96 of the tibia by pin 110 is shown in FIG. 19. To accommodate the upstanding central fin 16 of the femoral prosthesis 2, a reciprocating saw blade is located along the guide groove 100 of the tibial trial and the tibia moved about the femur through an arc of motion to cut a channel into the femur indicated by dotted line 112. In this way, the groove 100 of the tibial trial determines the correct orientation for fitting of the femoral prosthesis on the femur.

As an alternative, rather than cutting the channel into the femur as described above, a marker pen or diathermy can be used in place of the saw blade for marking of the femoral condyle for subsequent cutting of the channel into the femur using a saw blade in a free hand manner.

Figure 20:
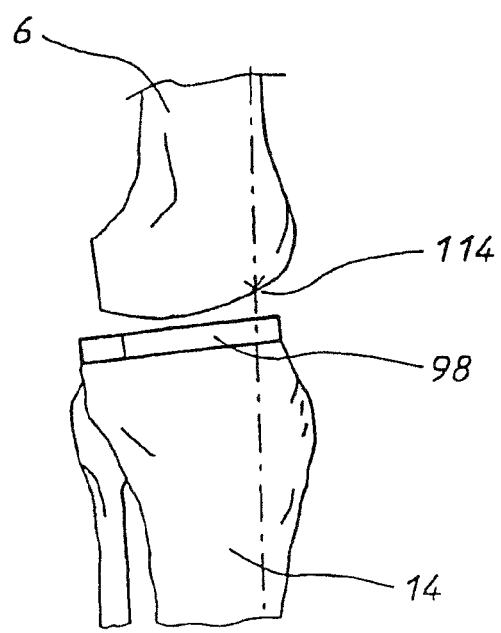
FIGS. 20 and 21 are diagrammatic views illustrating marking of a femoral condyle of the knee joint for further resection of the femur to enable fitting of the femoral prosthesis of FIG. 3.
Figure 21:
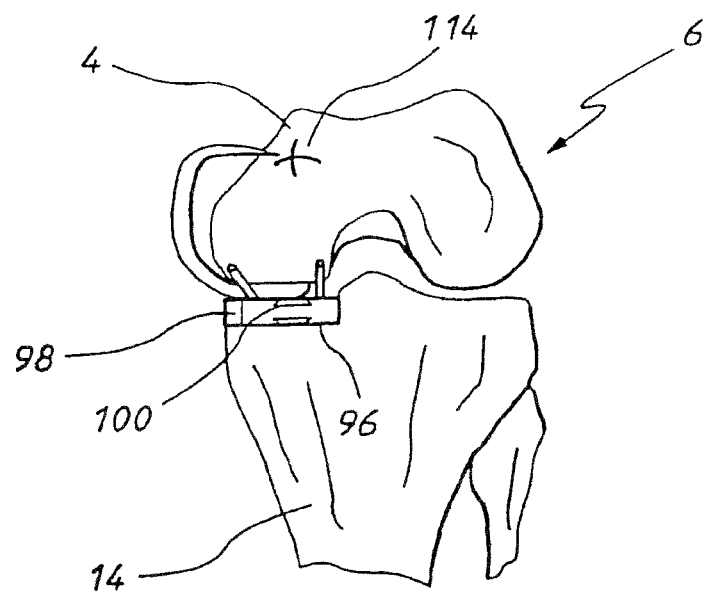

With the knee in full extension, and with care being taken not to hyperextend the knee, an imaginary line aligned with the groove 100 of the tibial trial is projected from the anterior side of the tibial trial 98 to the corresponding femoral medial condyle as indicated in FIG. 20. The point 114 at which the line strikes the femur is marked and corresponds to the optimal position of the anterior edge 116 of the femoral prosthesis 2, and is indicated more clearly in FIG. 21 where the tibia is shown in flexion relative to the femur.

Figure 22:
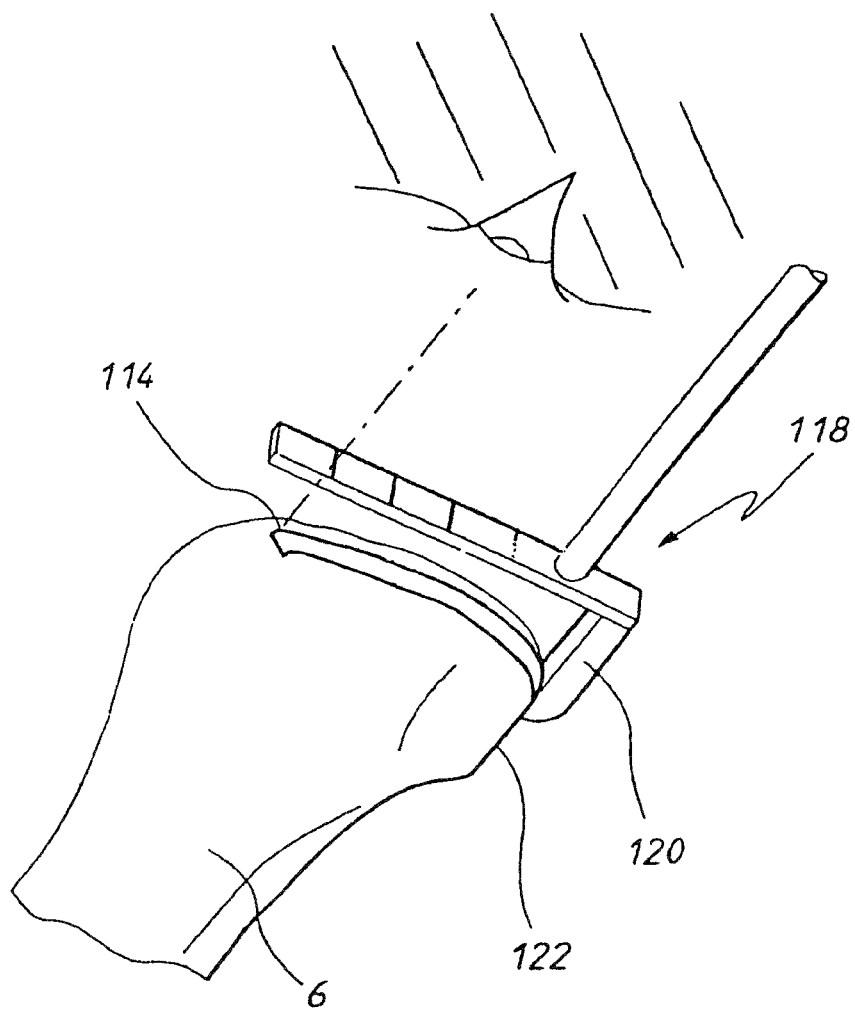
FIG. 22 is a diagrammatic view illustrating the use of a femoral sizer for determination of the appropriate sized femoral prosthesis.

A femoral sizer 118 is then aligned with the channel cut into the femur, with the posterior end 120 of the femoral sizer positioned flushly against the resected posterior face 122 of the femoral condyle, to allow determination of the required size of femoral prosthesis 2 by comparing the position of the mark 114 with calibrated markings on the femoral sizer as shown in FIG. 22.

Figure 23:
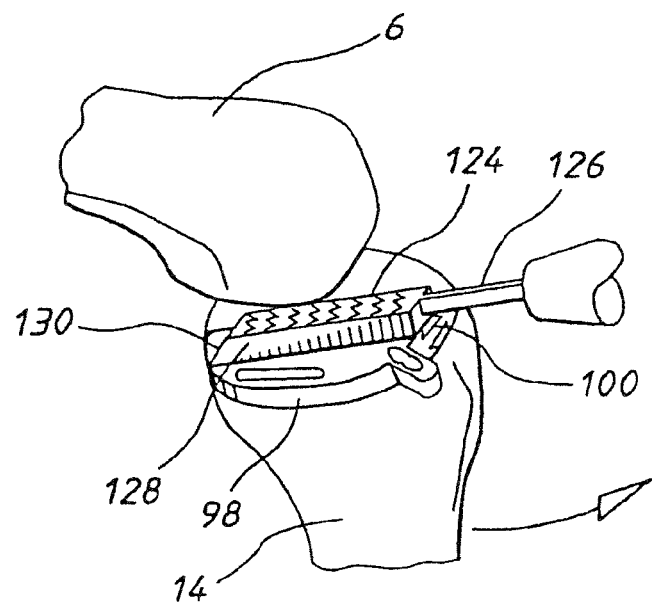
FIG. 23 is a diagrammatic view illustrating the use of a femoral shaping rasp for shaving bone from the relevant condyle of the femur to enable fitting of the femoral prosthesis.

The femoral condyle can then be sculpted as required to accommodate the fitting of the femoral prosthesis 2. This can be readily achieved with the use of a cutter device such as a femoral shaping rasp 124 illustrated in FIG. 23 or for instance, a router having a rotatable cutter for resecting bone from the femur. As can be seen, the rasp 124 has a tang 126 for being received by a reciprocating power saw. The body 128 of the rasp is generally flat and is provided with a tapered leading end 130. A key (not shown) extends centrally along the base of the rasp for reception in the guide groove 100 of the tibial trial 98. Accordingly, the groove of the tibial trial 98 acts to guide the reciprocating motion of the rasp when positioned on the tibial trial under the femur as illustrated in FIG. 23.

As will be understood, to sculpt the femur, the tibia is rotated about the femur through an arc of motion between forward and backward positions during which movement the cutting face of the rasp acts to progressively shave away the required thickness of the femur. It will also be appreciated that the thickness of the rasp is such to ensure that the original spacing between the femur and the tibia provided by the selected spacer 28 will be essentially retained upon the femoral prosthesis being fitted, for substantially maintaining the optimised balance in ligaments and other soft tissue initially provided by the spacing of the femur from the tibia by the selected spacer.

Figure 24:
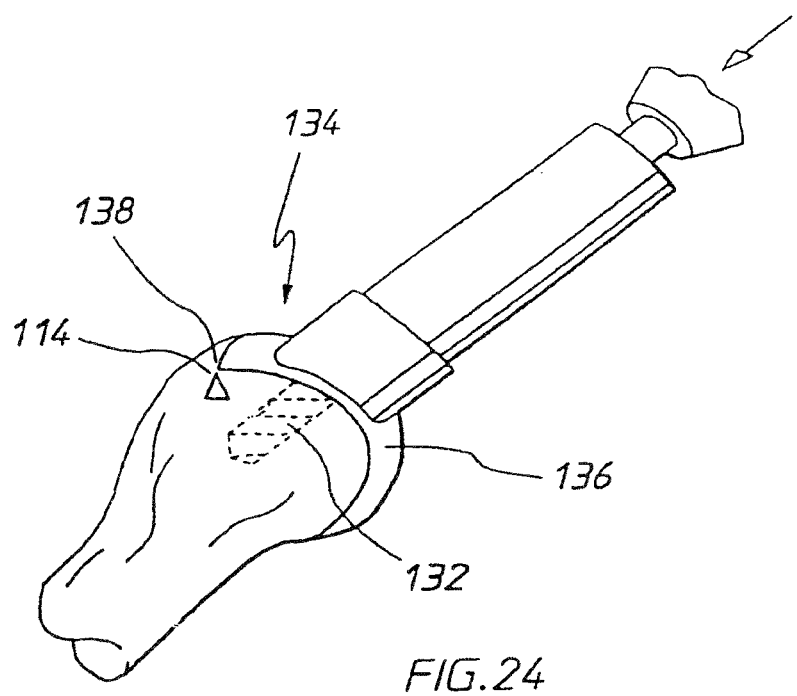
FIG. 24 is a diagrammatic view illustrating the use of a femoral peg drill guide to drill a bore into the femur for reception of the femoral peg of the femoral prosthesis shown in FIG. 3.

Drilling of the required bore 132 into the femur for reception of the peg 18 of the femoral prosthesis is readily achieved using a femoral peg drill guide 134 carrying a guide bracket 136 having a corresponding shape to the femoral prosthesis. Determination of the position for drilling the bore 132 is achieved by aligning the anterior tip 138 of the guide bracket 136 over the location 114 determined on the femur to correspond with the optimal positioning of the anterior end of the femoral prosthesis and reference is drawn to FIG. 24 for explanatory purposes.

Subsequently, the joint space is lavaged and a femoral trial affixed to the femur for a final assessment of joint stability and joint kinematics.

The tibial and femoral trials are then removed and the joint space thoroughly cleaned using pulsatile lavage prior to the tibial prosthesis 10 and the femoral prosthesis 2 being fixed to the tibia and the femur respectively, using appropriate conventionally known bonding cement such as polymethylacrylate bone cement. Prior to closing the wound the joint space is again thoroughly lavaged and if deemed necessary, local anaesthetic may be infiltrated at the wound site to assist post operative pain relief.

As will be appreciated, the tibial prosthesis used in a method as described herein may be selected from a number of such prostheses with a different thickness T to each other. The selected prosthesis will of course depend on the thickness of the spacer 28 required to initially optimise tension and balance in the action of the relevant ligaments and soft tissue structures of the knee joint during the movement of the tibia about the femur between forward and backward positions. For each thickness of tibial prosthesis, a corresponding cutting block 38 for guiding cutting of the tibia and the femur at the required spacing to accommodate the selected tibial prosthesis will be provided. Alternatively, a cutting block able to be adjusted to alter the spacing between the guide slots 60 and 62 as necessary to correspond to the thickness T of the selected tibial prosthesis may be used.

Figure 25:
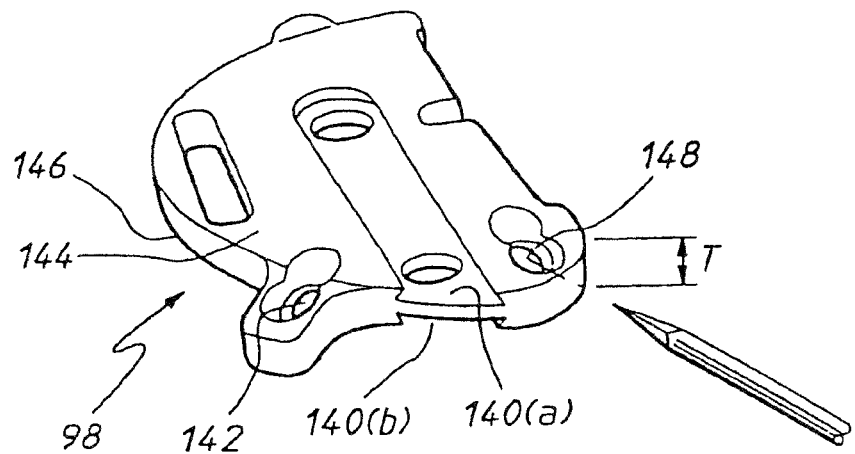
FIG. 25 is a perspective view of a tibial implant of the invention.
Figure 26:
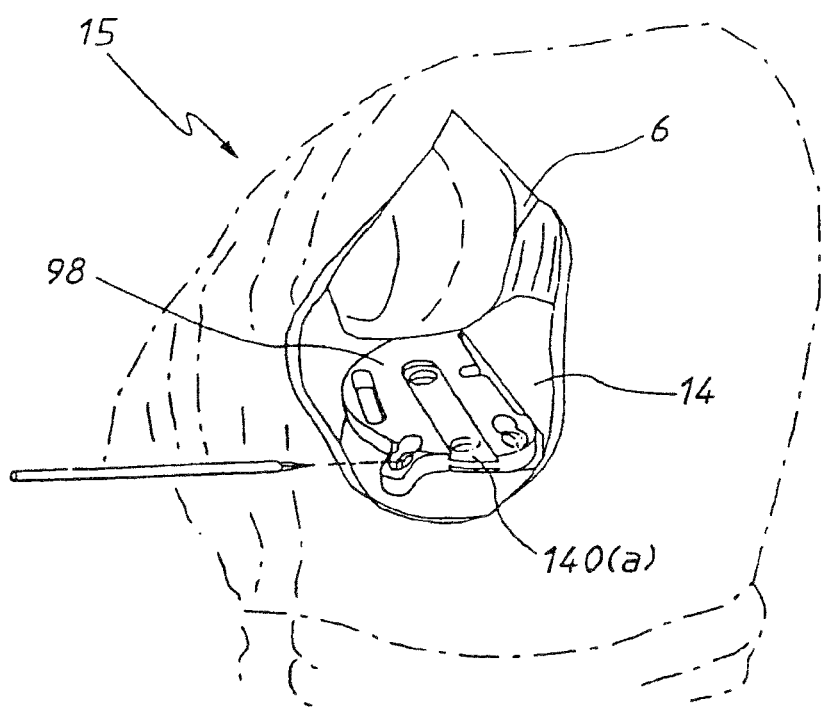
FIG. 26 is a diagrammatic view of the tibial implant of FIG. 25 fixed in position on the tibia.

Another embodiment of a tibial trial 98 having a guide channel 140(a) extending part way across the tibial trial in a generally anteroposterior direction is shown in FIG. 25 for reception of a router. The channel 140(a) has a dove tailed cross-section lying in a plane extending perpendicularly with respect to the major axis of the tibial trial. An identical channel 140(b) is defined in the underside of the tibial trial. As can be seen, this tibial trial is again provided with a channel 142 which extends from the upperside face 140 of the tibial trial through to its base 146 for reception of an obliquely orientated trocar pin therein for securing the tibial trial to the tibia. A further channel 148 is defined on the opposite side of the tibial trial for reception of an obliquely directed trocar pin. Indeed, the tibial trial is designed such that the tibial trial may be secured to either the medial condyle or the lateral condyle following the resection of bone therefrom. That is, by simply rotating the tibial trial 180° about its major axis the trial can be pinned to either medial lateral resected surfaces 96 of the tibia by the insertion of trocar pins through channels 142 and 148. The tibial trial when secured in position on the tibia prior to receiving the router is shown in FIG. 26.

Figure 27A:
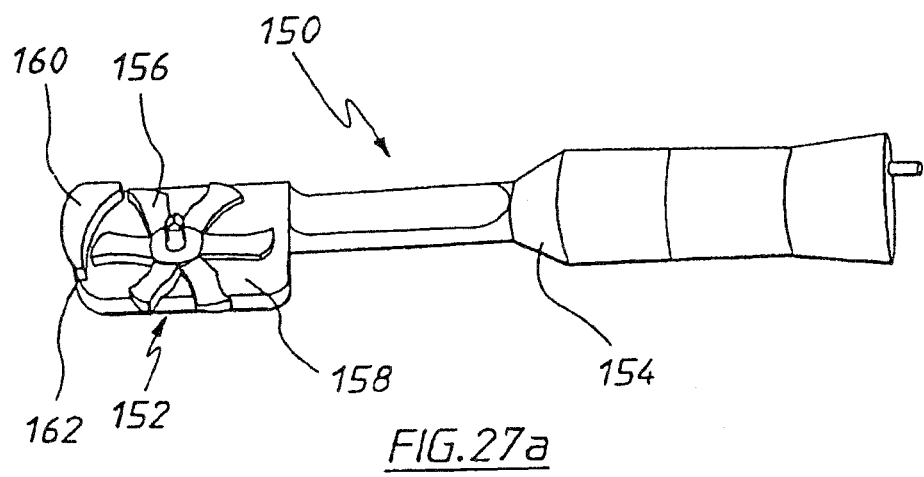
FIG. 27(a) is an elevated side view of a cutting device for resecting bone from the femur.
Figure 28:
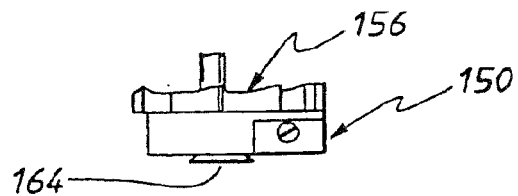
FIG. 28 is an end view of the cutting device of FIG. 27(a)
Figure 29:
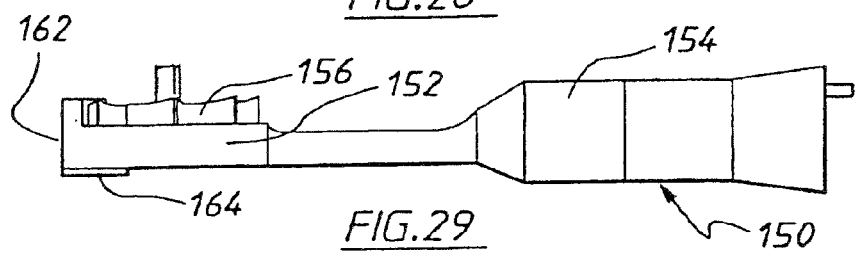
FIG. 29 is a side view of the cutting device of FIG. 27(a)

The router 150 shown in FIG. 27(a) comprises a flat head 152 having a substantially constant thickness along its length and which is detachably connected to body 154 of the router. A cutter disk 156 is seated in an aperture defined in the upperside 158 of the router head 152. A forward guard 160 is defined on the leading end 162 of the router. An end view of the router is shown in FIG. 28 and a side view in FIG. 29. As can be seen, a boss 164 having a dove tailed profile corresponding to that of the guide channel 140(a) of the tibial trial of FIG. 25 depends from the underside of the router 150 for reception in the guide channel 140(a) for thereby inhibiting lifting of the router from the tibial trial.

Figure 27B:
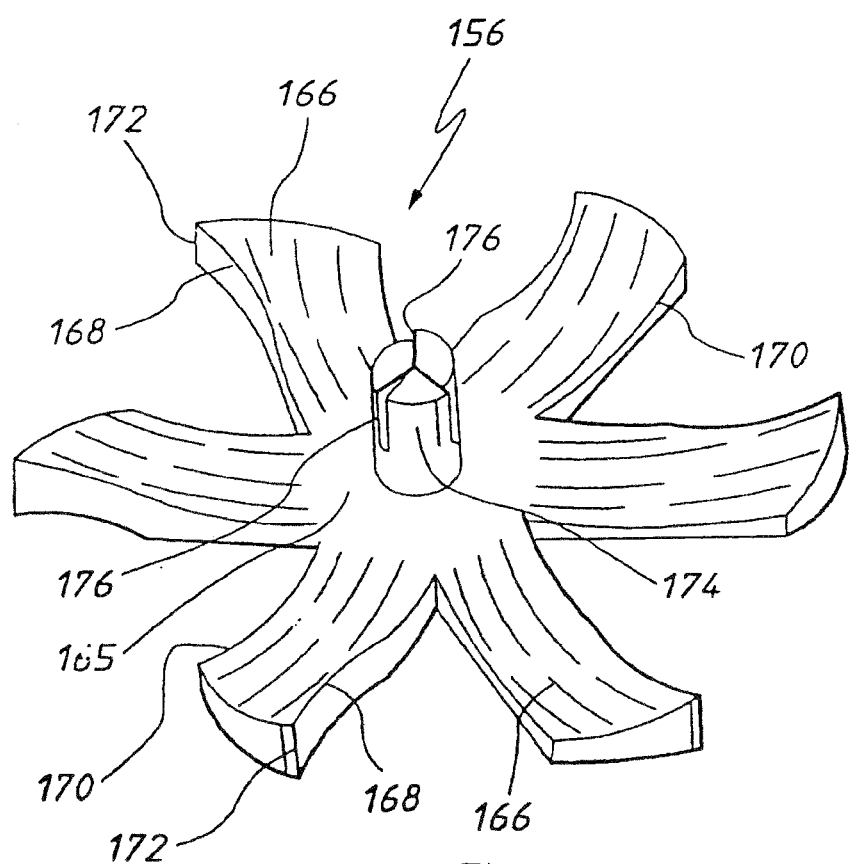
FIG. 27(b) is a perspective view of the cutter blade disk of the cutting device of FIG. 27(a)

The cutter disk 156 is more clearly shown in FIG. 27(b) and has a dished upper surface 165 and a plurality of radially directed blades 166. Each blade decreases in thickness from a leading cutting edge 168 to a trailing edge 170. A further cutting edge 172 is defined at the outer peripheral end of each blade. In addition, an integrally formed upstanding cutting blade 174 is centrally located on the cutter disk. The upstanding blade 174 has a plurality of upwardly directed cutting edges 176 spaced at 120° intervals around the blade. Specifically, the cutting edges 176 are defined on both the side and top end of the upstanding blade as can be seen.

Figure 30A:
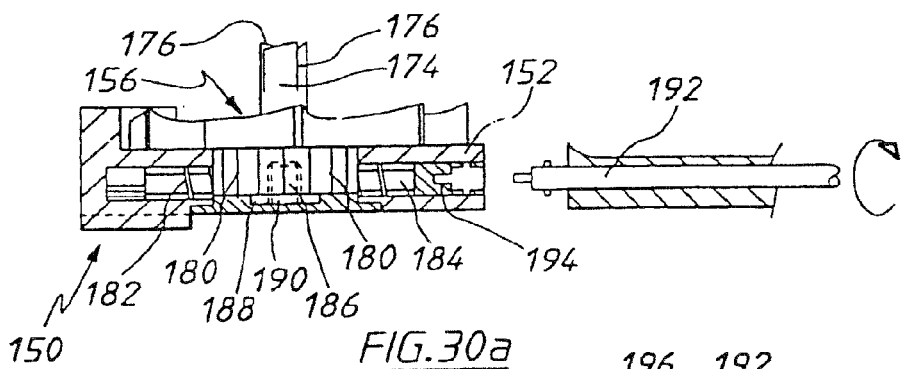
FIG. 30(a) is a longitudinal cross-sectional view of the cutting device of FIG. 27(a)

Turning now to FIG. 30(a), the cutter disk 156 further incorporates an integrally formed drive gear 178 with a plurality of vertically orientated teeth 180 which mesh with the screw of the screw drive 182 rotatably received within the head 152 of the router 150.

The cutter disk 156 has an internal female thread which mates with a screw 186 extending through collet 188 received in recess 190 defined in the underside of the router head, such that the cutter disk 156 is thereby retained in position on the router head and is rotatable with respect to the router head.

Figure 30B:
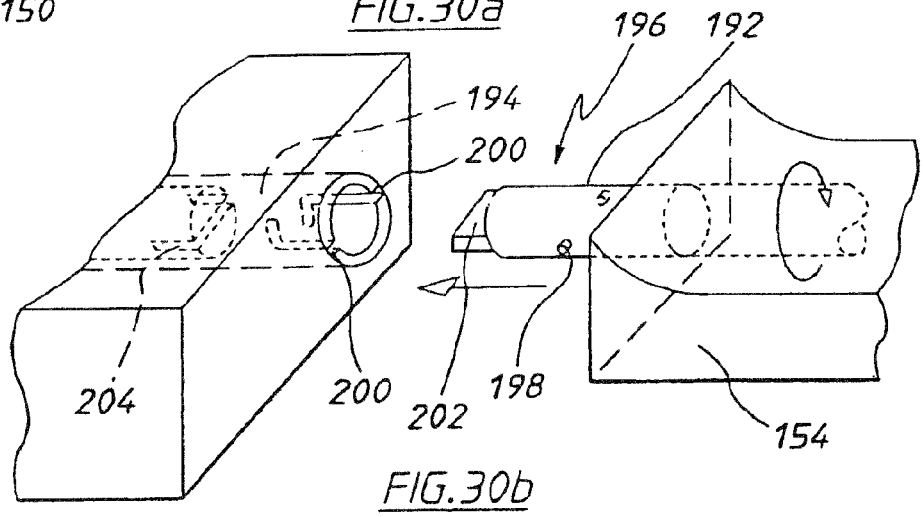
FIG. 30(b) is a diagrammatic partial view of a coupling arrangement used for coupling the head and body of the cutter device of FIG. 27(a) together.

A drive shaft 192 is rotatably mounted within the router body and projects therefrom for engagement with the female bayonet coupling 194 of the screw drive 184 of the router head. As shown in FIG. 30(b), the projecting end 196 of the drive shaft 192 carries bayonet pin 198 for reception in the bayonet recesses 200 of the bayonet coupling for thereby locking the router head 152 to the router body 154. The projecting end 196 of the drive shaft 192 is further provided with a flat drive projection 202 which slots into the slot 204 of the bayonet coupling for driving rotation of the screw drive 184 and so causing rotation of the cutter disk 156. The router body is adapted for being coupled with a power drive for driving rotation of the cutter disk typically in the range of from 5,000 rpm to about 7,000 rpm. As will be understood, once used, the router head 152 may be removed and discarded. Desirably, however, the body 154 of the router is sealed and is reusable following sterilisation.

Rather than engaging the cutter disk directly, the screw drive 184 of other embodiments may be arranged to drive a gear arrangement comprising a single gear or for instance a gear train incorporating a number of gears for driving the cutter disk. Alternatively, the router may incorporate a drive in the form of an endless belt, band or the like which upon being driven by the drive shaft causes rotation of the cutter disk.

As indicated above, the cutter disk 156 is freely rotatable with respect to the head of the router and may be lifted from the head upon the screw 186 being removed to allow replacement of the cutter disk with another of the same or different design. A blunt cutter disk may result in thermal necrosis of bone of the femur and accordingly it is desirable to replace the cutter disk if necessary. To assist in the insertion of the router into the knee joint, the leading end 162 of the head of the router has an arcuate profile.

Figure 31:
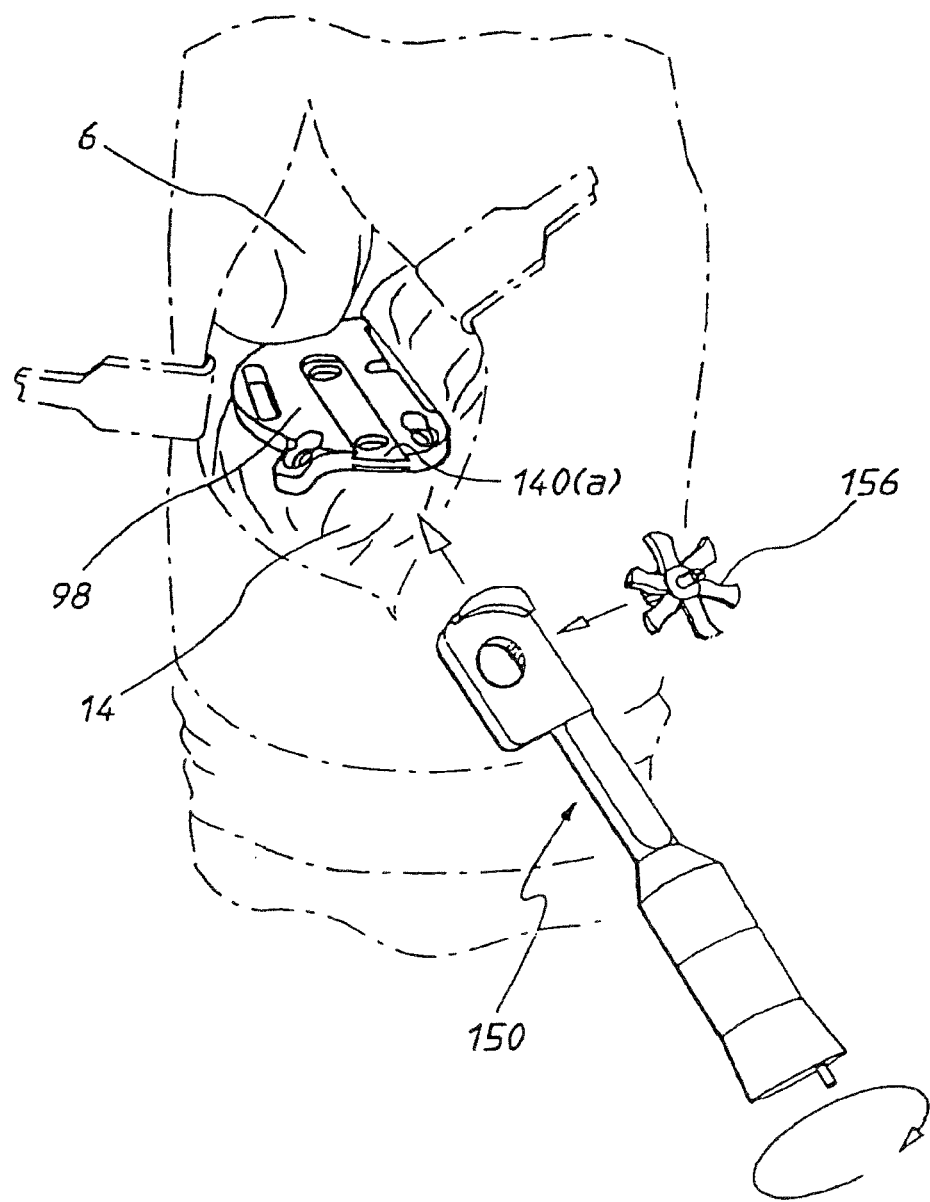
FIGS. 31 and 32 illustrate reception of the cutting device of FIG. 27(a) the tibial implant of FIG. 25 in unicondylar arthroplasty.
Figure 32:
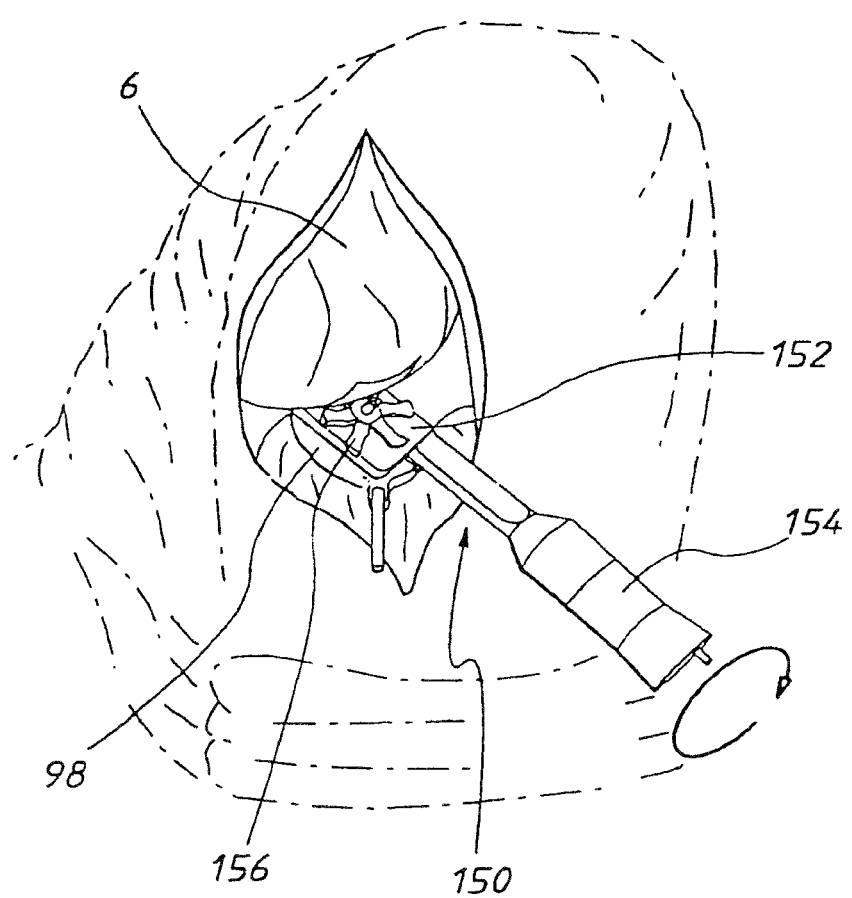

The insertion of the router into the knee joint is indicated in FIGS. 31 and 32, and the use of the tibial trial of FIG. 26 and router 150 in unicondylar knee arthroplasty is illustrated in FIGS. 33(a) to 33(c). Specifically, the tibia is again placed in flexion with respect to the femur, and the boss 164 of the router is inserted into the guide channel 140(a) of the tibial trial as shown in FIG. 32. Upon operation of the router and the tibia being moved about the femur through an arc of motion to an extended position, bone is resected from the femur to the desired depth in the direction of movement of the tibia as shown in FIG. 33(b). As indicated more clearly in FIG. 33(c), the channel 206 for reception of the central fin 16 of the femoral prostheses is simultaneously cut into the femoral condyle by upstanding blade 174 of the cutter disk 156 of the router 150.

Rather than cutting the channel 206 for reception of the central fin of the femoral prosthesis simultaneously with the resurfacing of the femur utilising the cutter disk 156, the resurfacing of the femur and the cutting of the channel 206 may be achieved in a two stage process. That is, a cutter blade may be located in the router for cutting the channel in an initial step, and then that cutter blade replaced with one for resecting the required thickness of bone from the femur and which incorporates an upstanding centrally located non-cutting boss for reception in the cut channel 206 to thereby guide the resurfacing of the femur. In this instance, the boss will generally be of a height such that a space remains between the upper end of the boss and the overlying roof of the channel.

Similarly, rather than resecting the posterior chamfer from the femur with a reciprocating saw utilising the cutting block 38 for guidance, the posterior chamfer may be resected from the femur with the use of a router 150 in which the router head 152 is provided without a guard 160. As such, a cutting block may be provided that while being capable of being coupled with the spacer selected for optimum spacing of the femur from the tibia as described above, may only be adapted for guiding cutting of the tibia at the relevant depth therein and not the femur.

While the method has been described in relation to arthroplasty performed on the medial condyles of the tibia and the femur, unicondylar arthroplasty may be performed on the lateral condyles in the same manner.

In addition, rather than removing the entire upper segment of the relevant condyle of the tibia in unicondylar arthroplasty to provide an exposed recess on which the tibial trial and subsequently the final tibial prosthesis 10 is onset and fixed in position as described above, a recess may be formed in the condyle into which the tibial trial and ultimately the tibial prosthesis are inset, respectively. An apparatus for providing such a recess in the tibia is shown in FIG. 34.

The apparatus comprises a router 208 and a guide jig 210 for guiding the router to form the inset recess 212, in this case in the medial condyle of the tibia 14.

The router 208 has an elongated body 214 housing a drive shaft 216 for driving rotation of a router blade 218 in the same manner as described for the router shown in FIG. 30, for resecting the bone from the tibia to the desired depth in the tibia. The drive shaft 216 projects from the trailing end 222 of the body 214 for reception by a power tool for driving rotation of the drive shaft.

A guide pin 224 projects from an underside of the router body 214 for reception in a recessed template 226 defined in the floor of channel 228 of the guide jig 210. A recessed area is also defined in the body of the router to allow the router to overlie the rim 232 of the recess and to allow the router blade to resect the bone from the tibia to the desired depth. The guide pin has a length to ensure reception in the recessed template of the guide jig when the router is positioned over the tibia prior to commencement of the resection of bone in the formation of the recess. Similarly, the depth of the recessed template is sufficient to ensure the entire exposed length of the guide pin is able to be accommodated therein.

The profile of the template 226 substantially matches the external profile of the tibial trial to be used, and the template is dimensioned for the recess to be of a size sufficient to allow the tibial trial to be seated on the resected tibial surface 96 at the base of the recess. Once received in the recess, the surrounding bone of the tibia acts to inhibit the tibial trial and subsequently the actual tibial prosthesis 10 from being transversely dislocated.

In order to position the guide jig 210 about the knee, the tibiofemoral cutting block 38 is firstly arranged adjacent to the tibia in the manner described above utilising the selected spacer 28 to determine the position of the cutting block with respect to the tibia, prior to the securing of the cutting block in position using trocar pins 234. As will be understood, trocar pins 234 are dimensioned for being inserted into the channels 84 and 90 of the cutting block and alignment component in a sliding fit and to allow the cutting block and alignment component 68 to be slid from the pins following resection of the one or both of the tibia and femur as described above.

Once the cutting block and spacer assembly has subsequently been slid from the trocar pins the guide jig 210 is slid onto the trocar pins 234 such that the trocar pins are received in longitudinally extending parallel channels 236 of the guide jig.

The router blade 218 projects from the head 220 of the router a distance such that when the router is received in the channel 228 of the guide jig, bone is able to be resected from the tibia to a depth corresponding to the position of the bottom 72 of the lower slot 64 of the cutting block 38 prior to removal of the cutting block from the tibia. Resection of bone from the tibia beyond this depth is inhibited by abutment of the underside surface 238 of the rear end region 240 of the router with the floor 242 of the channel of the guide jig. To resect bone from the tibia to greater depths to accommodate different sized tibial trials, different sized router blades may be utilised on the router.

In order to enhance stability, the guide jig is provided with a rest 244 that projects downwardly from the leading end 246 of the guide jig and which rests against the leg of the patient to thereby assist in maintaining the jig in position at the angle in the anterior to posterior direction determined by the alignment component 68. The guide jig is secured in position on the tibia by pin 248 inserted into the tibia through channel 250 defined in the rest 244 which channel extends at an oblique angle with respect to parallel channels 236 of the guide jig receiving trocar pins 234.

The recess 212 in the tibia is formed and shaped by the application of downward pressure to the router as the router is moved side to side and forward and backward in the guide jig, the movement of the router across the tibia being limited by the restricted field of movement of the guide pin in the recessed template of the jig. Accessible tibial osteophytes may be removed prior to or following the formation of the recess in the tibia. To allow for the resection of differently sized recesses, a range of guide jigs may be provided with templates of different width and length dimensions. Similarly, the location of the guide pin 224 on the router may be adjustable along the router to accommodate resection of the recess in the desired position on the tibia, or otherwise the guide jig may be adapted for facilitating adjustment of the position of the guide jig along the trocar pins. This may be achieved for instance by the rest being extendible relative to the remainder of the guide jig for causing the desired displacement of the template away from the knee joint.

The tibia trial when seated in the recess will typically protrude above the rim 232 of the recess. Usually, the tibial trial will be secured in position in the recess by an appropriately located pin inserted into the tibia at an oblique angle (not shown).

The channel for receiving the central fin 16 of the femoral prosthesis may then be cut into the corresponding condyle of the femur if not already achieved simultaneously during the resection of the femur with the use of a router of the type shown in FIG. 30.

Rather than utilising a guide jig arrangement of the type shown in FIG. 34 for resecting a channel into the tibia for insertion of a tibial trial and subsequently a tibial prosthesis therein, apparatus as shown in FIG. 8 may more desirably be utilised. In this instance, rather than the cutting block 38 being mounted on the rearward tongue 66 of the alignment component 68, the cutting block is rotated 180° and mounted on the forward tongue 76 of the alignment component as indicated in the exploded view shown in FIG. 35 and the view of the assembled arrangement indicated in FIG. 36. Accordingly, in this instance the alignment component 68 is located between the cutting block 38 and the tibia 14 for resection of the posterior chamfer from the femur 6 as indicated above. Once the posterior chamfer has been resected, the cutting block 38 is slid from the alignment component 68 leaving the alignment component 68 behind in position relative to the tibia.

The body 74 of the alignment component is dimensioned such that the upper surface 252 of the head 254 is aligned at the same level as the bottom of the middle slot 62 of the cutting block for the spacer, prior to the cutting block being slid from the trocar pins securing the alignment component in position relative to the tibia. The upper surface 252, therefore, may therefore be used as a rest for a router 256 as shown in FIG. 37 for removing bone from the tibia to form a recess to the desired depth for the seating therein of a tibial trial and thereafter the ultimate tibial prosthesis. That is, the height of the cutter blade 258 of the router 256 is dimensioned such that the floor of the recess resected into the tibia is at a level corresponding to the level of the bottom 72 of the lower slot 64 of the cutting block when located in position adjacent to the tibia. As with the cutter blade of the router shown in FIG. 30, the cutter blade 258 has cutting edges defined on both the sides and top end of the blade.

The correct size of the recess to be resected is firstly ascertained by locating different tibial trial templates on the tibial condyle and selecting the most appropriate one prior to marking the profile of the selected templated on the tibial trial in the required location with methylene blue or other suitable dye as is conventionally known in the art.

Following removal of the alignment component 68 for insetting of the tibial trial in the resected recess, the femur may be further resected as described above for the fitting of the femoral prosthesis.

Another router employing a cutter disk 260 is shown in FIG. 38. This embodiment rather than being adapted for reception by a tibial trial, has a body 262 with a head 264 adapted for being seated on the base of the recess 212 resected into the tibia and which is dimensioned such that movement of the router when in position in the recess in a generally medial to lateral direction or vice versa is limited. The cutter disk is the same as that utilised on the router shown in FIG. 30 and is arranged for resection of the femur to the desired depth in that bone in the manner described above upon movement of the tibia through an arc of motion about the femur.

In a bicondylar knee arthroplasty method, two small stab incisions are made in the knee with a scalpel blade to provide portals for insertion of a spacer in each one, respectively. The incisions are located medial and lateral to the patellar tendon to allow access to between the tibia and the femur, and are positioned so as to generally not coincide with ligamentous and other soft tissue structures of the knee.

A spacer is then introduced between the opposing lateral condyles and the opposing medial condyles of the tibia and the femur, respectively. The desired thickness of spacers required to obtain balance in the action of relevant ones of the ligaments and other soft tissue structures of the knee during flexion and extension of the tibia relative to the femur to provide appropriate tension in the knee joint and correction of varus or valgus deformity is determined substantially as described above using different thicknessed spacers.

Specifically, the tibia is moved about the femur between forward and backward positions and the kinematics of the knee evaluated. If necessary, one or both of the spacers may be substituted with one(s) of a different thickness and movement of the knee joint while the spacers are in position checked again. This may be repeated a number of times until the optimum spacing of the femur from the tibia is obtained. Accordingly, the spacers selected for optimum spacing of the femur from the tibia may have the same thickness as each other or a different thickness to each other depending on the degree of spacing required between the respective condyle pairs.

The spacers will usually be linked together by a cross-bar during the rotation of the tibia about the femur. The cross-bar may comprise a stiff metal member secured to each spacer by a clamp or suitable fastener respectively, or other such arrangement for inhibiting independent movement of the spacers.

In this way, the desired balancing and deformity correction of the knee joint may be achieved prior to surgically opening the medial and lateral compartments of the knee joint for resection of the medial and lateral condyles of the femur and the tibia.

Once the spacers for providing the optimum spacing of the femur and the tibia have been selected, unicondylar arthroplasty is performed on each of the medial and lateral condyle pairs as described above, one pair at a time. Preferably, the condyle pair deemed to require the greater degree of deformity correction is subjected to arthroplasty first.

More particularly, bone may be resected from the tibia utilising either the tibiofemoral cutting block 38 or guide jig 210 to guide the resection of the bone. Once both the tibial and femoral trials have been fitted, arthroplasty is then performed on the other of the condyle pairs.

Prior to doing so, the spacer selected for spacing of those condyles apart is reinserted between them and the kinematics of the knee joint checked by rotating the tibia about the femur to confirm satisfactory kinematics of the knee joint. Bone is then resected from the tibial and femoral condyles of that pair to the desired depth in each one again utilising the spacer as reference for the positioning of the tibiofemoral cutting block 38 or guide jig 210. Upon fitting of the further tibial and femoral trials, the kinematics of the knee joint are checked once again to ensure adequate range of motion and retention of optimum tension in ligaments and other soft tissue structures of the knee joint. The respective tibial trials and femoral trials are subsequently removed and replaced with the final tibial and femoral prostheses. Generally, the tibial and femoral prostheses will be fitted to one condyle pair at a time.

Accordingly, the bicondylar knee arthroplasty method described comprises performing unicondylar knee arthroplasty as described herein on both medial and lateral condyle pairs of the knee. As will be further appreciated, the bicondylar arthroplasty method involves gently retracting the patella transversely about the knee joint to gain access to the medial or lateral compartment of the knee joint and, subsequently retracting the patella transversely about the knee joint in the opposite direction to gain access to the other of the knee compartments. The method may also allow the quadricep system to remain substantially intact.

Moreover, as with the unicondylar arthroplasty technique described, the bicondylar knee arthroplasty method may allow the desired tensioning and deformity correction to be achieved substantially without the need to transect, elevate or release soft tissue structures of the knee joint although again, adjustment prior to or following fitting of the tibial and femoral trials is not excluded.

Accordingly, although the present invention has been described hereinbefore with reference to preferred embodiments, the skilled addressee will understand that numerous variations and modifications are possible without departing from the scope of the invention.

We claim:

1. A spacer to balance tension in ligaments and other soft tissue structures of a knee joint comprising a femur and a tibia, the spacer comprising:
    an elongate handle; and
    a leading end region extending from the elongate handle and configured for insertion into the knee joint, the leading end region having a contour dimensioned for engagement with one of medial or lateral condyles of the femur and a corresponding one of medial or lateral condyles of the tibia, the leading end region defining a thickness dimensioned to obtain a desired spacing between the femur and the tibia, and wherein the thickness of the leading end region is greater adjacent the elongate handle relative to a forward-most end of the leading end region, wherein the leading end region has an upperside and an opposite underside, the upperside defining a contoured upper surface dimensioned for engagement with the one of the medial or lateral condyles of the femur, the underside defining an under surface dimensioned for engagement with the corresponding one of the medial or lateral condyles of the tibia, wherein the contoured upper surface comprises a concave trough that is dimensioned to receive the one of the medial or lateral condyle of the femur.

2. The spacer according to claim 1, wherein the upperside defines a raised ridge with the concave trough extending forward of the raised ridge.

3. The spacer according to claim 1, wherein the upperside defines a raised ridge and the contoured upper surface extending forward of the raised ridge.

4. The spacer according to claim 3, wherein the raised ridge extends transversely across the upperside of the leading end region.

5. The spacer according to claim 1, wherein the underside defines a protrusion extending from the under surface and dimensioned for engagement with the tibia.

6. The spacer according to claim 1, further comprising a set of the spacers each having a different thickness dimensioned to obtain different spacings between the femur and the tibia.

7. The spacer according to claim 1, further comprising:
    a first of the spacer configured for engagement between opposing medial condyles of the femur and the tibia, the leading end region of the first spacer defining a first thickness dimensioned to provide a first spacing between the opposing medial condyles; and
    a second of the spacer configured for engagement between the opposing lateral condyles of the femur and the tibia, the leading end region of the second spacer defining a second thickness dimensioned to provide a second spacing between the opposing lateral condyles; and
    wherein the first thickness of the first spacer and the second thickness of the second spacer are dimensioned to provide optimal balance tension in the ligaments and other soft tissue structures of the knee joint; and
    wherein the first and second spacers are dimensioned for simultaneous insertion into the knee joint to balance tension in ligaments and other soft tissue structures of the knee joint.

8. The spacer according to claim 7, wherein the first thickness of the first spacer is different from the second thickness of the second spacer.

9. A system to balance tension in ligaments and other soft tissue structures of a knee joint comprising a femur and a tibia, the system comprising:
    a spacer, comprising:
        an elongate handle; and
        a leading end region extending from the elongate handle and configured for insertion into the knee joint, the leading end region having a contour dimensioned for engagement with one of medial or lateral condyles of the femur and a corresponding one of medial or lateral condyles of the tibia, the leading end region defining a thickness dimensioned to obtain a desired spacing between the femur and the tibia, and wherein the thickness of the leading end region is greater adjacent the elongate handle relative to a forward-most end of the leading end region; and
    a cutting guide, wherein the elongate handle is removably coupled with the cutting guide to guide the cutting of one or both of the tibia and the femur, the cutting guide comprising:
        a first passageway configured to guidingly receives a cutting tool to guide the cutting of one or both of the tibia and the femur; and
        a second passageway that receives the elongate handle of the spacer to thereby couple the cutting guide to the spacer.

10. The system according to claim 9, wherein the leading end region includes an upper surface dimensioned for the direct contact with the one of medial or lateral condyles of the femur.

11. The system according to claim 10, wherein the upper surface of the leading end region is contoured and dimensioned to receive the one of medial or lateral condyles of the femur.

12. A spacer to balance tension in ligaments and other soft tissue structures of a knee joint comprising a femur and a tibia, the spacer comprising:
   an elongate handle; and
   a leading end region extending from the elongate handle and configured for insertion into the knee joint to obtain a desired spacing between the femur and the tibia, the leading end region having an upperside and an opposite underside, the upperside defining a raised ridge and a contoured upper surface forward of the raised ridge that is dimensioned for engagement with one of medial or lateral condyles of the femur, the underside defining an under surface dimensioned for engagement with a corresponding one of medial or lateral condyles of the tibia, the underside further defining a protrusion extending from the undersurface and dimensioned for engagement with the tibia, wherein the contoured upper surface comprises a trough that is dimensioned to receive the one of the medial or lateral condyles of the femur.

13. The spacer according to claim 12, wherein the contoured upper surface is scooped forward of the raised ridge to define a concave trough dimensioned to receive the one of the medial or lateral condyles of the femur.

14. The spacer according to claim 12, wherein the raised ridge extends transversely across the upperside of the leading end region.

15. The spacer according to claim 12, wherein the under surface is contoured for engagement with the corresponding one of the medial or lateral condyles of the tibia.

16. The spacer according to claim 12, wherein the leading end region has a thickness between the upperside and the underside that is dimensioned to space the femur a distance from the tibia at the desired spacing; and
   further comprising a set of the spacers each having a different thickness dimensioned to obtain different spacings between the femur and the tibia.

17. The spacer according to claim 12, further comprising:
   a first of the spacer configured for engagement between opposing medial condyles of the femur and the tibia, the leading end region of the first spacer defining a first thickness dimensioned to provide a first spacing between the opposing medial condyles; and
   a second of the spacer configured for engagement between the opposing lateral condyles of the femur and the tibia, the leading end region of the second spacer defining a second thickness dimensioned to provide a second spacing between the opposing lateral condyles; and
   wherein the first thickness of the first spacer and the second thickness of the second spacer are dimensioned to provide optimal balance tension in the ligaments and other soft tissue structures of the knee joint; and
   wherein the first and second spacers are dimensioned for simultaneous insertion into the knee joint to balance tension in ligaments and other soft tissue structures of the knee joint.

18. The spacer according to claim 17, wherein the first thickness of the first spacer is different from the second thickness of the second spacer.

19. A spacer to balance tension in ligaments and other soft tissue structures of a knee joint comprising a femur and a tibia, the spacer comprising:
   an elongate handle; and
   a leading end region extending from the elongate handle and configured for insertion into the knee joint to obtain a desired spacing between the femur and the tibia, the leading end region having an upperside and an opposite underside, the upperside defining a raised ridge and a contoured upper surface forward of the raised ridge that is dimensioned for engagement with one of medial or lateral condyles of the femur, the underside defining an under surface dimensioned for engagement with a corresponding one of medial or lateral condyles of the tibia, the underside further defining a protrusion extending from the undersurface and dimensioned for engagement with the tibia, wherein the contoured upper surface comprises a concavity that is dimensioned to receive the one of the medial or lateral condyles of the femur.

20. A system to balance tension in ligaments and other soft tissue structures of a knee joint comprising a femur and a tibia, the system comprising:
   a spacer, comprising:
      an elongate handle; and
      a leading end region extending from the elongate handle and configured for insertion into the knee joint to obtain a desired spacing between the femur and the tibia, the leading end region having an upperside and an opposite underside, the upperside defining a raised ridge and a contoured upper surface forward of the raised ridge that is dimensioned for engagement with one of medial or lateral condyles of the femur, the underside defining an under surface dimensioned for engagement with a corresponding one of medial or lateral condyles of the tibia, the underside further defining a protrusion extending from the undersurface and dimensioned for engagement with the tibia; and
   a cutting guide, wherein the elongate handle is removably coupled with the cutting guide to guide the cutting of one or both of the tibia and the femur, the cutting guide comprising:
      a first passageway configured to guidingly receives a cutting tool to guide the cutting of one or both of the tibia and the femur; and
      a second passageway that receives the elongate handle of the spacer to thereby couple the cutting guide to the spacer.

21. The system according to claim 20, wherein the contoured upper surface of the leading end region is dimensioned to receive one of medial or lateral condyles of the femur.

22. The system according to claim 20, wherein the under surface of the leading end region is dimensioned for receipt within the corresponding one of the medial or lateral condyles of the tibia.

23. A set of spacers to balance tension in ligaments and other soft tissue structures of a knee joint comprising a femur and a tibia, the set of spacers comprising:
   a first spacer configured for direct contact with opposing medial condyles of the femur and the tibia, the first spacer having a leading end region defining a first thickness dimensioned to provide a first spacing between the opposing medial condyles; and
   a second spacer configured for direct contact with opposing lateral condyles of the femur and the tibia, the second spacer having a leading end region defining a second thickness dimensioned to provide a second spacing between the opposing lateral condyles; and
   wherein the first thickness of the first spacer and the second thickness of the second spacer are dimensioned to provide optimal balance tension in the ligaments and other soft tissue structures of the knee joint;
   wherein the leading end region of each of the first and second spacers has an upperside and an opposite underside, the upperside defining a raised ridge and a contoured upper surface forward of the raised ridge that is dimensioned for engagement with a corresponding one of the medial and lateral condyles of the femur, the underside defining an under surface dimensioned for engagement with a corresponding one of the medial and lateral condyles of the tibia; and wherein the contoured upper surface comprises a concave trough that is dimensioned to receive the corresponding one of the medial and lateral condyles of the femur.

24. A set of spacers to balance tension in ligaments and other soft tissue structures of a knee joint comprising a femur and a tibia, the set of spacers comprising:

a first spacer configured for engagement between opposing medial condyles of the femur and the tibia, the first spacer having a leading end region defining a first thickness dimensioned to provide a first spacing between the opposing medial condyles; and a second spacer configured for engagement between the opposing lateral condyles of the femur and the tibia, the second spacer having a leading end region defining a second thickness dimensioned to provide a second spacing between the opposing lateral condyles; and wherein the first thickness of the first spacer and the second thickness of the second spacer are dimensioned to provide optimal balance tension in the ligaments and other soft tissue structures of the knee joint; and wherein the first spacer and the second spacer are dimensioned for simultaneous insertion into the knee joint to balance tension in ligaments and other soft tissue structures of the knee joint.

25. The set of spacers according to claim 24, wherein the leading end region of each of the first and second spacers has an upperside and an opposite underside, the upperside defining a raised ridge and a contoured upper surface forward of the raised ridge that is dimensioned for engagement with a corresponding one of the medial and lateral condyles of the femur, the underside defining an under surface dimensioned for engagement with a corresponding one of the medial and lateral condyles of the tibia.

26. The set of spacers according to claim 25, wherein the contoured upper surface comprises a concave trough that is dimensioned to receive the corresponding one of the medial and lateral condyles of the femur.

27. The set of spacers according to claim 25, wherein the raised ridge extends transversely across the upperside of the leading end region.

28. The set of spacers according to claim 24, wherein the first spacer includes a contoured upper surface dimensioned to receive the medial condyle of the femur, and wherein the second spacer includes a contoured upper surface dimensioned to receive the lateral condyle of the femur.

29. The set of spacers according to claim 24, wherein the first thickness of the first spacer is different from the second thickness of the second spacer.

30. A set of spacers to balance tension in ligaments and other soft tissue structures of a knee joint comprising a femur and a tibia, the set of spacers comprising:

a first spacer configured for engagement between opposing medial condyles of the femur and the tibia, the first spacer having a leading end region defining a first thickness dimensioned to provide a first spacing between the opposing medial condyles; and a second spacer configured for engagement between the opposing lateral condyles of the femur and the tibia, the second spacer having a leading end region defining a second thickness dimensioned to provide a second spacing between the opposing lateral condyles; and wherein the first thickness of the first spacer and the second thickness of the second spacer are dimensioned to provide optimal balance tension in the ligaments and other soft tissue structures of the knee joint; and wherein the leading end region of the first and second spacers has an upperside and an opposite underside, the upperside defining a concave upper surface defining a trough dimensioned to receive one of the medial and lateral condyles of the femur, the underside defining an under surface dimensioned for engagement with a corresponding one of the medial and lateral condyles of the tibia.

31. The set of spacers according to claim 30, wherein each of the first and second spacers includes an elongate handle extending from the leading end region.

32. The set of spacers according to claim 31, wherein a thickness of the leading end region of each of the first and second spacers is greater adjacent the elongate handle relative to a forward-most end of the leading end region.

33. A set of spacers according to claim 31, wherein the elongate handle is dimensioned to protrude from the knee joint when the leading end region is inserted into the knee joint; and wherein the elongate handle is dimensioned to couple with a cutting guide configured to guide the cutting of one or both of the tibia and the femur, the cutting guide comprising:

a first passageway configured to guidingly receives a cutting tool to guide the cutting of one or both of the tibia and the femur; and a second passageway that receives the elongate handle of the spacer to thereby couple the cutting guide to the spacer.

34. The set of spacers according to claim 30, wherein the underside defines a protrusion extending from the under surface and dimensioned for engagement with the tibia.

* * * * *